(12) United States Patent  
Bauhahn et al.

(10) Patent No.: US 9,789,324 B2
(45) Date of Patent: Oct. 17, 2017

(54) EXTERNAL ENERGY TRANSFER SYSTEM FOR AN IMPLANTABLE MEDICAL DEVICE AND METHOD THEREFOR

(71) Applicant: MEDTRONIC, INC., Minneapolis, MN (US)

(72) Inventors: Ruth E. Bauhahn, Fridley, MN (US); Mark E. Schommer, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/985,700

(22) Filed: Dec. 31, 2015

(65) Prior Publication Data

US 2016/0193471 A1    Jul. 7, 2016

Related U.S. Application Data

(62) Division of application No. 13/687,560, filed on Nov. 28, 2012, now Pat. No. 9,259,584, which is a division of application No. 10/958,191, filed on Oct. 4, 2004, now Pat. No. 8,346,361.

(60) Provisional application No. 60/513,732, filed on Oct. 23, 2003, provisional application No. 60/508,198, filed on Oct. 2, 2003.

(51) Int. Cl.
*A61N 1/378* (2006.01)
*A61N 1/372* (2006.01)

(52) U.S. Cl.
CPC ....... *A61N 1/3787* (2013.01); *A61N 1/37229* (2013.01); *A61N 1/37247* (2013.01)

(58) Field of Classification Search
CPC .. A61N 1/372; A61N 1/37235; A61N 1/3787; A61N 1/37247
USPC .......................................... 607/30, 34, 60, 61
See application file for complete search history.

(56) References Cited

U.S. PATENT DOCUMENTS

| 2003/0014087 A1* | 1/2003 | Fang | A61N 1/025 |
| | | | 607/48 |
| 2005/0021108 A1* | 1/2005 | Klosterman | A61N 1/3605 |
| | | | 607/48 |

* cited by examiner

*Primary Examiner* — Michael Carey
(74) *Attorney, Agent, or Firm* — Withers & Keys, LLC

(57) ABSTRACT

User interface for external power source, recharger, for an implantable medical device. At least some of patient controls and display icons of an energy transfer unit are common with at least some of the patient controls and the display icons of a patient control unit. An energy transfer unit is operable by the patient with less than three operative controls to control energy transfer from the external energy transfer unit to the implantable medical device. An external antenna having a primary coil can inductively transfer energy to a secondary coil of the implantable medical device when the external antenna is externally placed in proximity of the secondary coil. An energy transfer unit has an external telemetry coil allowing the energy transfer unit to communicate with the implantable medical device through the internal telemetry coil in order to at least partially control the therapeutic output of the implantable medical device.

51 Claims, 31 Drawing Sheets

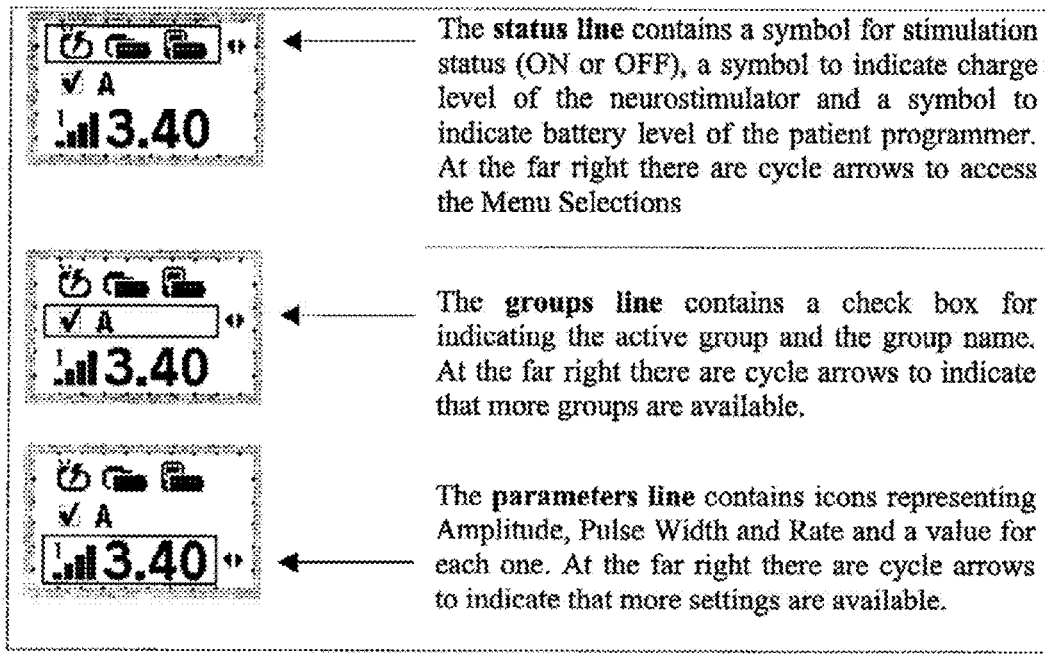
Figure 5 Therapy Status Screen
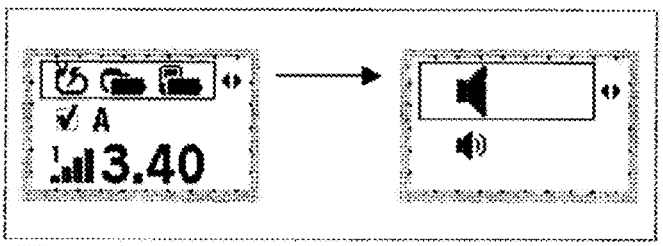
Figure 6 Access to Menu Selections
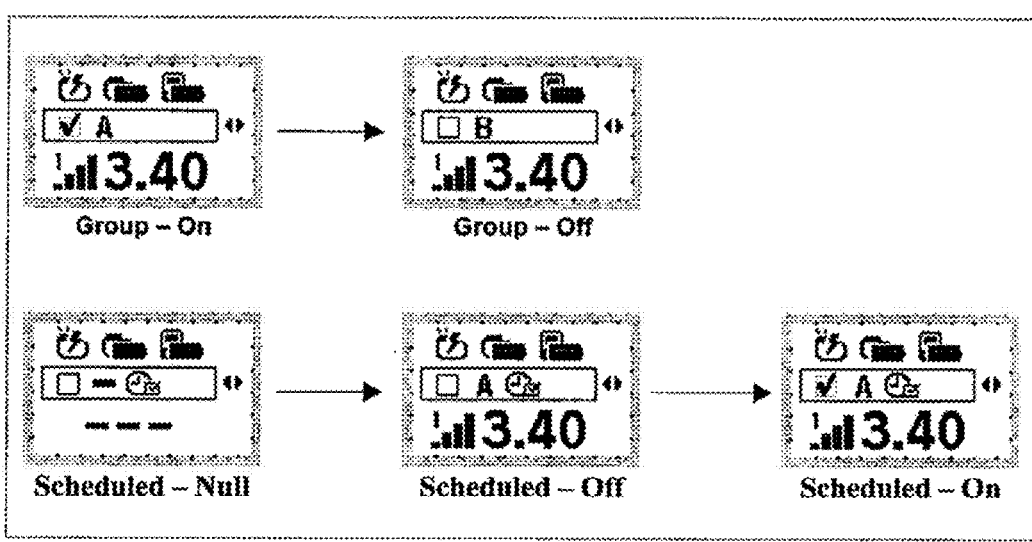
Figure 7 Group Selections

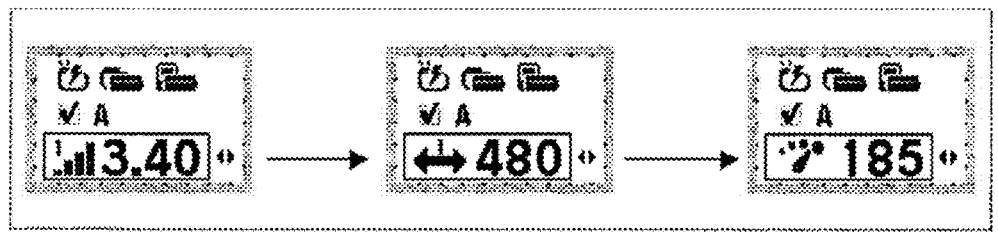
Figure 8 Parameter Selections
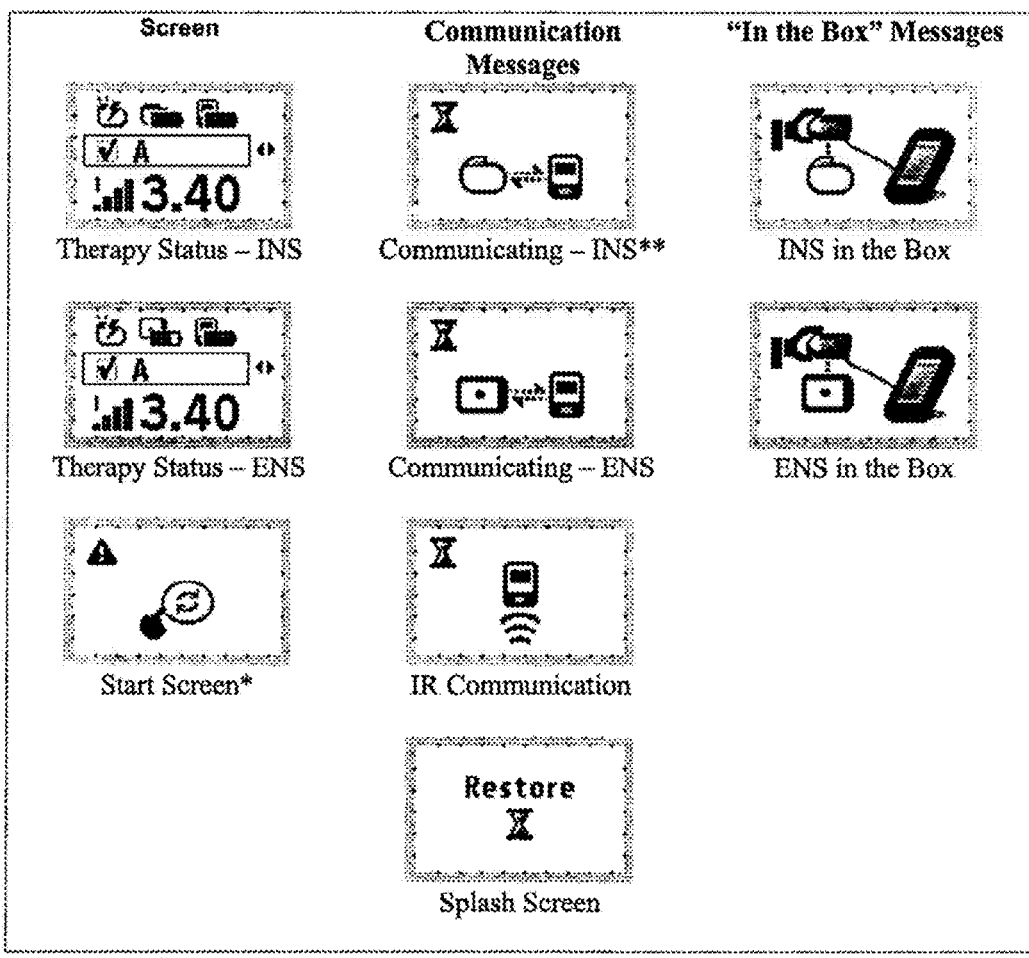
Figure 9A Screens

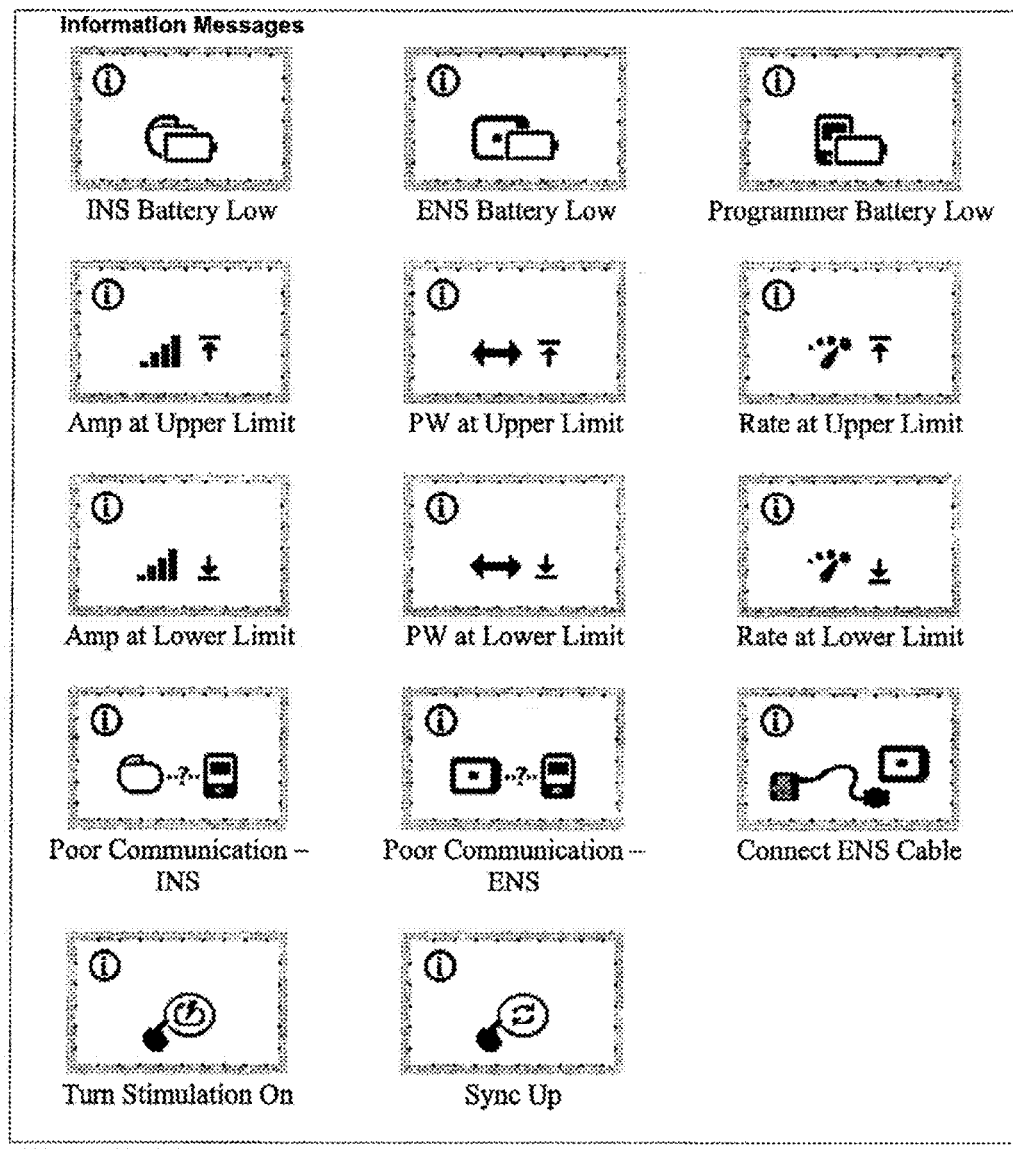
Figure 9B Messages

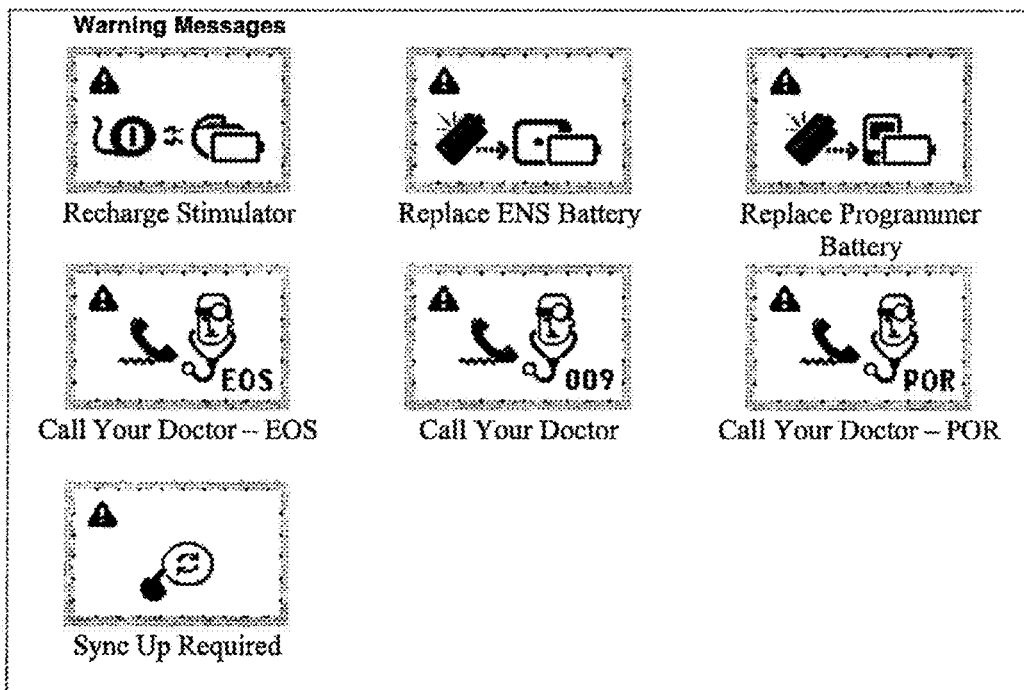
Figure 9C Warnings
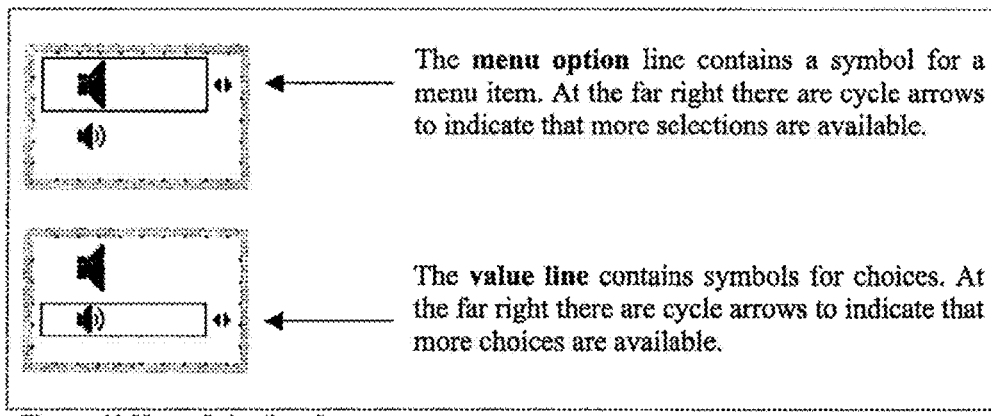
Figure 10 Menu Selection Screen

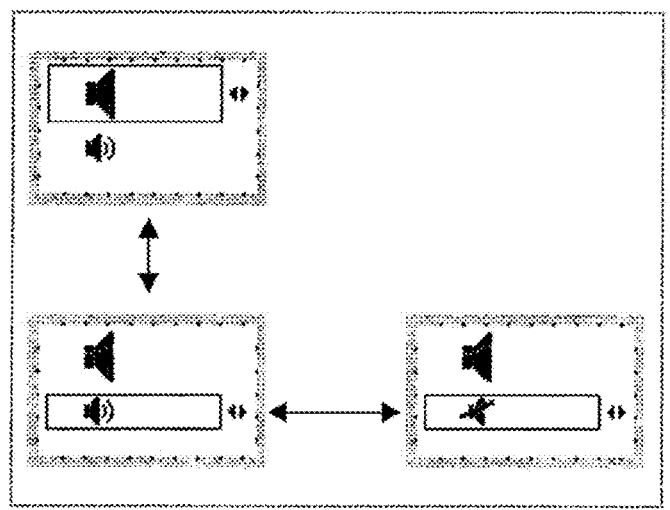
Figure 11 Audio
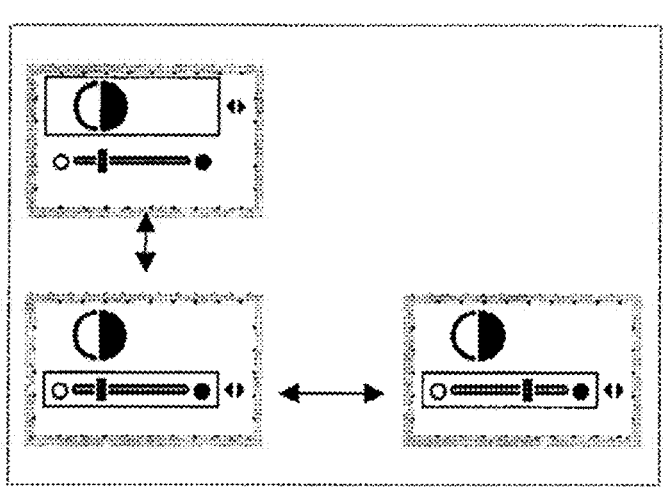
Figure 12 Contrast

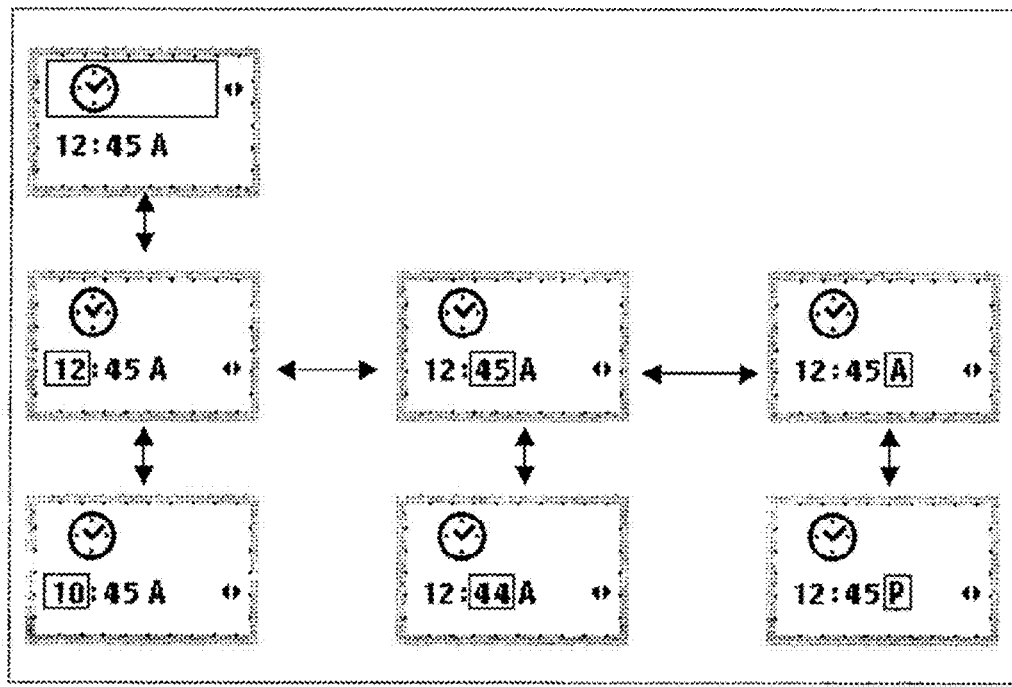
Figure 13 INS/ENS Time
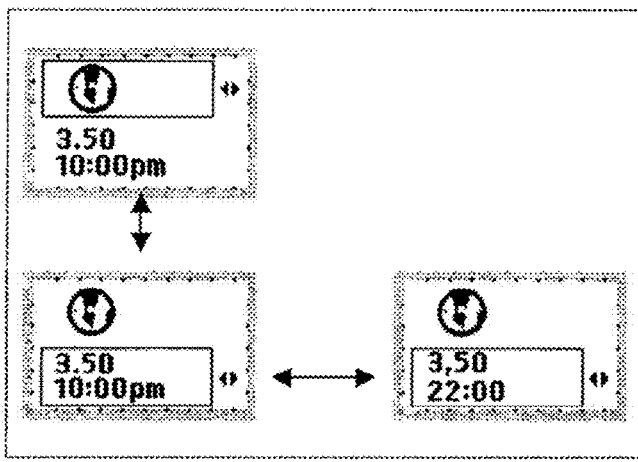
Figure 14 Time/Number Formats

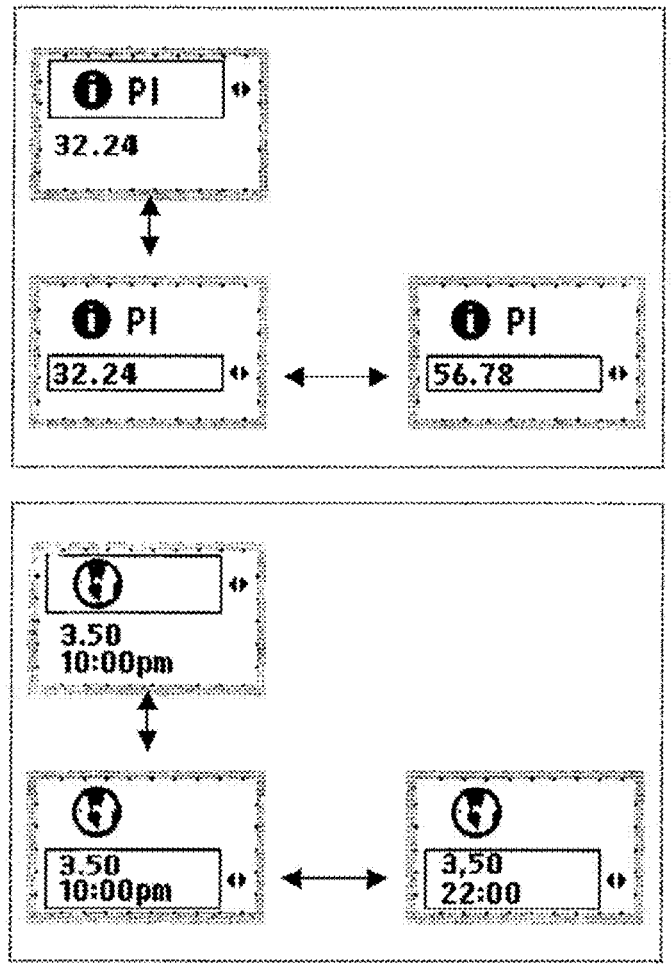
Figure 15 Patient Programmer Information
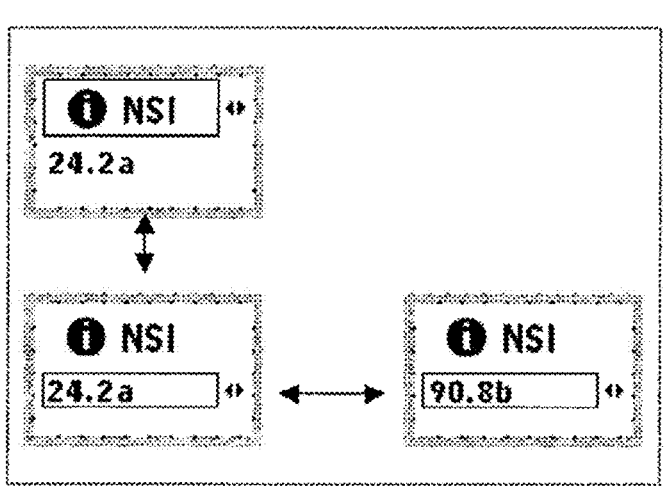
Figure 16 INS/ENS Information

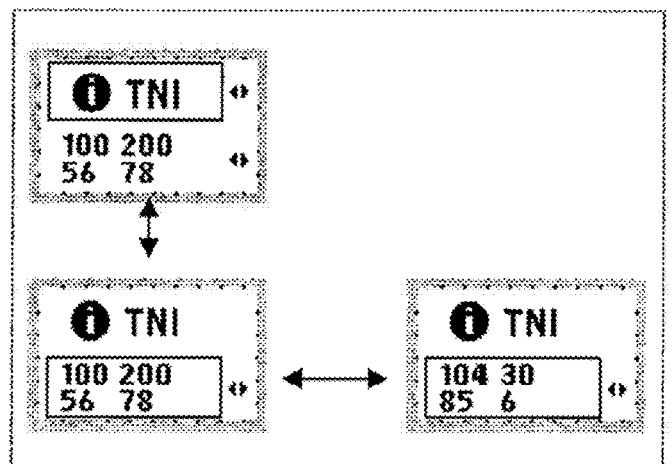
Figure 16A Telemetry N Information

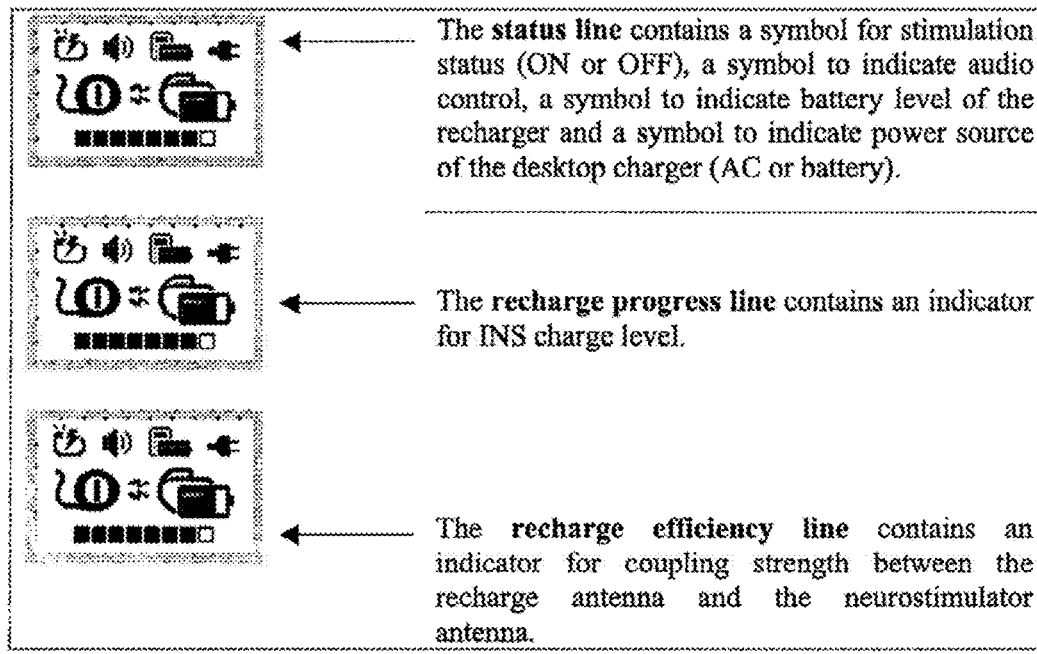
Figure 19 INS Charge Status Screen
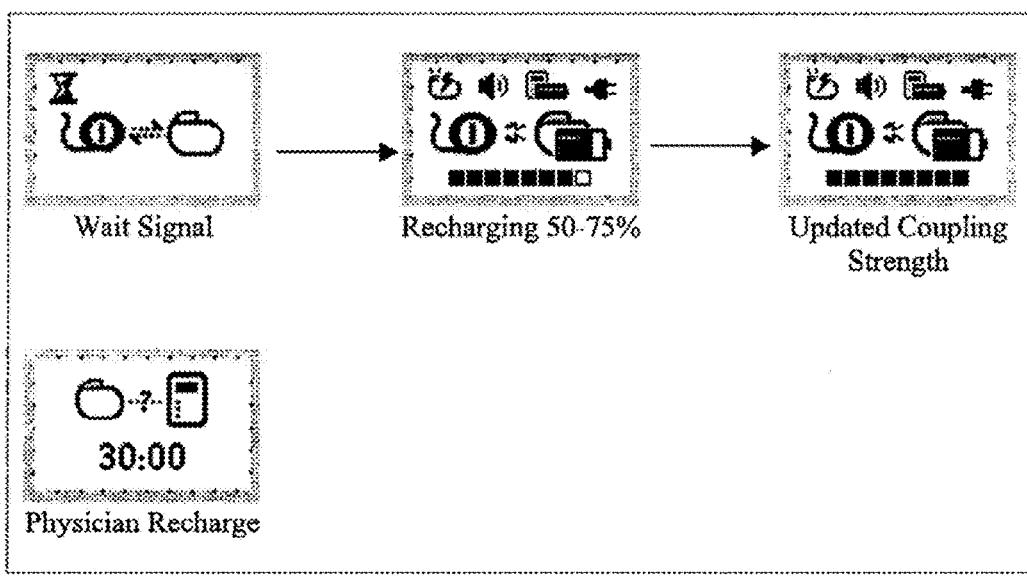
Figure 20 Recharging the INS

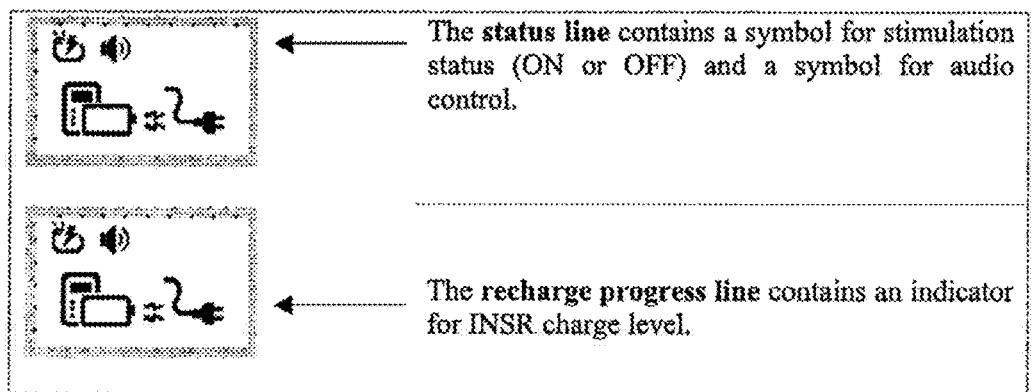
Figure 21 INSR Charge Status Screen
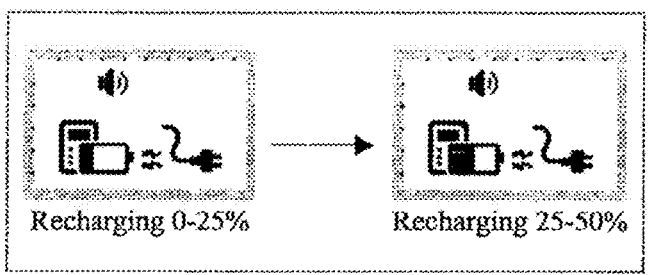
Figure 22 Recharging the INSR

| SCREENS | INFORMATION MESSAGES* | WARNING MESSAGES** |
|---|---|---|
| POWER DOWN | INS BATTERY LOW | RECHARGE STIMULATOR |
| START SCREEN - NOT DOCKED | INS RECHARGE INTERRUPTED | REPOSITION ANTENNA - PRESS START CHARGE |
| START SCREEN - DOCKED | INS RECHARGE COMPLETE | REPOSITION ANTENNA - PRESS THERAPY OFF |
| WAIT SCREEN | INSR BATTERY LOW | REPOSITION ANTENNA - PRESS THERAPY ON |
| INS CHARGE STATUS | INSR RECHARGE COMPLETE | RECHARGE INSR |
| INSR CHARGE STATUS | INSR RECHARGE INTERRUPTED | CONNECT INSR ANTENNA |

SCREENS, INFORMATION MESSAGES AND WARNINGS

Fig. 23A

| Name | Label | Function |
|---|---|---|
| Power button | ⏻ | - Turn display on and off<br>- Turn backlight on when held down |
| Therapy On | | - Turn therapy on<br>- Turn display on if pressed when programmer is powered down |
| Therapy Off | | - Turn therapy off<br>- Turn display on if pressed when programmer is powered down. |
| Increase | ✚ | - Change values |
| Decrease | ▬ | - Change values |
| Sync | ⟳ | - Interrogate the implanted device; activate a group<br>- Turn display on if pressed when programmer is powered down. |
| Scroll Up/Down | ▲ ▼ | - Select displayed items |
| Scroll Left/Right | ◀ ▶ | - Access available choices for a selected item |

Fig. 24

Table 1 Icons for Status Line

| Name | File | Icon | Size | Coordinates |
|---|---|---|---|---|
| Status Line Box | Box_17x78 | | 80w x 19h | R0 C2 |
| Stim On | status_stim_on | | 16w x 15h | R2 C9 |
| Stim Off | status_stim_off | | 16w x 15h | R2 C9 |
| INS Batt1 | status_ins_battery_100 | | 22w x 15h | R2 C29 |
| INS Batt2 | status_ins_battery_75 | | 22w x 15h | R2 C29 |
| INS Batt3 | status_ins_battery_50 | | 22w x 15h | R2 C29 |
| INS Batt4 | status_ins_battery_25 | | 22w x 15h | R2 C29 |
| INS Batt5 | status_ins_battery_0 | | 22w x 15h | R2 C29 |
| Programmer Batt1 | status_ppg_battery_100 | | 21w x 15h | R2 C55 |
| Programmer Batt2 | status_ppg_battery_75 | | 21w x 15h | R2 C55 |
| Programmer Batt3 | status_ppg_battery_50 | | 21w x 15h | R2 C55 |
| Programmer Batt4 | status_ppg_battery_25 | | 21w x 15h | R2 C55 |
| Programmer Batt5 | status_ppg_battery_0 | | 21w x 15h | R2 C55 |
| ENS Batt1 | status_ens_battery_100 | | 22w x 15h | R2 C29 |
| ENS Batt2 | status_ens_battery_75 | | 22w x 15h | R2 C29 |
| ENS Batt3 | status_ens_battery_50 | | 22w x 15h | R2 C29 |
| ENS Batt4 | status_ens_battery_25 | | 22w x 15h | R2 C29 |
| ENS Batt5 | status_ens_battery_0 | | 22w x 15h | R2 C29 |
| Small Arrow | small_arrow | | 10w x 8h | R6 C83 |

Fig. 25

Table 2 Icons for Groups Line

| Name | File | Icon | Size | Coordinates |
|---|---|---|---|---|
| Groups Line Box | box_15x78 |  | 80w x 17h | R18 C2 |
| Check Off | check_off |  | 12w x 13h | R20 C9 |
| Check On | check_on | ✓ | 12w x 13h | R20 C9 |
| Scheduled Therapy | scheduled_therapy |  | 18w x 13h | R20 C40 |
| Null Set | null_set | — | 12w x 5h | R24 C25 |
| Small Arrow | small_arrow | ◆ | 10w x 8h | R22 C83 |
| Group Labels |  | -- | -- | R21 C26 |

Fig. 26

Table 3 Icons for Parameters Line

| Name | File | Icon | Size | Coordinates |
|---|---|---|---|---|
| Parameters Line Box | box_22x78 |  | 80w x 24h | R34 C2 |
| Amp1 | Amplitude_1 |  | 21w x 18h | R38 C7 |
| Amp2 | Amplitude_2 |  | 21w x 18h | R38 C7 |
| Amp3 | Amplitude_3 |  | 21w x 18h | R38 C7 |
| Amp4 | Amplitude_4 |  | 21w x 18h | R38 C7 |
| PW1 | Pulsewidth_1 |  | 26w x 18h | R37 C7 |
| PW2 | Pulsewidth_2 |  | 26w x 18h | R37 C7 |
| PW3 | Pulsewidth_3 |  | 26w x 18h | R37 C7 |
| PW4 | Pulsewidth_4 |  | 26w x 18h | R37 C7 |
| Rate | Rate |  | 23w x 18h | R37 C9 |
| Decimal | decimal | . | 6w x 6h | R50[a] |
| Comma | Comma | , | 7w x 7h | R49[a] |
| Num0 | number_0 | 0 | 13w x 19h | R37[b] |
| Num1 | number_1 | 1 | 7w x 19h | R37[b] |
| Num2 | number_2 | 2 | 13w x 19h | R37[b] |
| Num3 | number_3 | 3 | 14w x 19h | R37[b] |
| Num4 | number_4 | 4 | 14w x 19h | R37[b] |
| Num5 | number_5 | 5 | 13w x 19h | R37[b] |
| Num6 | number_6 | 6 | 13w x 19h | R37[b] |
| Num7 | number_7 | 7 | 13w x 19h | R37[b] |
| Num8 | number_8 | 8 | 13w x 19h | R37[b] |
| Num9 | number_9 | 9 | 13w x 19h | R37[b] |
| Null Value | Null_set_value | --- | 40w x 5h | R43 C22 |
| Small Arrow | small_arrow | ↔ | 10w x 8h | R42 C83 |

Fig. 27

Table 4 Icons for Information Messages and Cautions

| Name | File | Icon | Size | Coordinates |
|---|---|---|---|---|
| Wait Signal | msg_wait_signal | | 14w x 16h | R3 C5 |
| Communicating | msg_communicate | | 59w x 23h | R26 C18 |
| Communicating – ENS | msg_communicate_ens | | 61w x 23h | R26 C18 |
| All cautions | msg_ppg_information | | 17w x 17h | R3 C5 |
| INS Battery Low | msg_ins_battery_low | | 36w x 24h | R27 C30 |
| ENS Battery Low | msg_ens_battery_low | | 43w x 23h | R28 C26 |
| Programmer Battery Low | msg_ppg_battery_low | | 36w x 26h | R26 C30 |
| Amp at Upper Limit | msg_upper_limit_amplitude | | 40w x 17h | R30 C28 |
| PW at Upper Limit | msg_upper_limit_pulsewidth | | 44w x 14h | R32 C26 |
| Rate at Upper Limit | msg_upper_limit_rate | | 41w x 18h | R30 C27 |
| Amp at Lower Limit | msg_low_limit_amplitude | | 41w x 17h | R30 C27 |
| PW at Lower Limit | msg_low_limit_pulsewidth | | 43w x 14h | R32 C26 |
| Rate at Lower Limit | msg_low_limit_rate | | 41w x 18h | R30 C27 |
| Poor Communication | msg_poor_communication | | 59w x 23h | R26 C18 |
| Poor Communication – ENS | msg_poor_communication_ens | | 61w x 23h | R26 C18 |
| Sync Up | msg_sync | | 36w x 29h | R24 C30 |
| Stim On | msg_stim_on | | 36w x 29h | R24 C30 |
| Codes for Call Your Doctor | Med 15pt font | -- | -- | R44,C** |
| IR Communication* | msg_ir_communication | | 22w x 40h | R14, C37 |
| Connect ENS Cable | msg_cable_problem | | 78w x 31h | R23 C9 |

Fig. 28

Table 5 Icons for Warnings

| Name | File | Icon | Size | Coordinates |
|---|---|---|---|---|
| All warnings | msg_ppg_attention | | 16w x 14h | R4 C5 |
| Recharge Stimulator | msg_recharge_stim | | 82w x 24h | R26 C7 |
| Replace ENS Battery | msg_ens_battery_depleted | | 79w x 27h | R24 C8 |
| Replace Programmer Battery | msg_ppg_battery_depleted | | 72w x 27h | R14 C12 |
| Sync Up Required | msg_sync | | 36w x 29h | R23 C30 |
| Turn Stimulation On | msg_turn_stim_on | | 36w x 29h | R23 C30 |
| Call Your Doctor | msg_call_your_doctor | | 57w x 43h | R8 C19 |
| Codes for Call Your Doctor | Med 15pt font | -- | -- | R44, C** |
| Sync Up – Start | msg_sync | | 36w x 29h | R15 C30 |
| Text for Splash* | Med 15pt font | | -- | R14, C23 |
| Wait Signal Splash* | msg_wait_signal | | 14w x 16h | R28 C41 |

Fig. 29

Table 6 Icons for Menu Selections

| Name | File | Icon | Size | Coordinates |
|---|---|---|---|---|
| Box for Menu Selections[1] | menu_box_26x78 | | 80w x 28h | R0 C2 |
| Box for Contrast, Audio and System Info Values | menu_box_16x78 | | 80w x 18h | R29 C2 |
| Box for INS/ENS Time Values | menu_box_16x21 | | 23w x 18h | R30 C[3] |
| Box for INS/ENS Time – AM/PM | menu_box_16x13 | | 15w x 18h | R30 C47 |
| Box for Time/Number Format and Telemetry N Information Values | menu_box_27x78 | | 80w x 29h | R29 C2 |
| Small arrows | small_arrow | | 10w x 8h | R[2], C83 |
| Audio | menu_audio | | 15w x 24h | R2 C19 |
| Audio | menu_audio_on | | 17w x 14h | R31 C19 |
| Audio | menu_audio_off | | 17w x 14h | R31 C19 |
| Contrast | menu_contrast | | 26w x 24h | R2 C15 |
| Contrast | menu_slide | | 72w x 9h | R34 C6 |
| Contrast | menu_slider | | 6w x 12h | R32 C[4] |
| INS/ENS Time | menu_clock | | 24w x 24h | R2 C13 |
| Values for Hours/Minutes | Med 15 pt font | -- | -- | R35 C[5] |
| Colon – INS/ENS Time | menu_colon | : | 4w x 8h | R36 C24 |
| Time/Number Format | menu_time_number | | 24w x 24h | R2 C14 |
| Number – OUS Value | number_comma | 1,000.00 | 54w x 13h | R31 C9 |
| Number – US Value | number_decimal | 1,000.00 | 54w x 13h | R31 C9 |
| Time – 12h Value | menu_time12h_format | 10:00pm | 51w x 13h | R43 C9 |
| Time – 24h Value | menu_time24h_format | 22:00 | 36w x 11h | R44 C9 |
| System Info | menu_info[6] | | 19w x 19h | R5 C13 |
| System Info Values | Med15pt font[7] | -- | -- | -- |

Fig. 30

Table 12 Icons for Status Line

| Name | File | Icon | Size | Coordinates |
|---|---|---|---|---|
| INSR Wait Signal | msg_insr_wait_signal | | 14w x 16h | R3 C5 |
| Therapy On | status_stim_on | | 16w x 16h | R1 C6 |
| Therapy Off | status_stim_off | | 16w x 16h | R1 C6 |
| Audio On | status_beep_on | | 17w x 14h | R3 C27 |
| Audio Off | status_beep_off | | 17w x 14h | R3 C27 |
| INSR Batt1 | status_hhp_battery_100 | | 21w x 15h | R2 C49 |
| INSR Batt2 | status_hhp_battery_75 | | 21w x 15h | R2 C49 |
| INSR Batt3 | status_hhp_battery_50 | | 21w x 15h | R2 C49 |
| INSR Batt4 | status_hhp_battery_25 | | 21w x 15h | R2 C49 |
| INSR Batt5 | status_hhp_battery_0 | | 21w x 15h | R2 C49 |
| Power Source Symbol | status_plug | | 16w x 11h | R6 C75 |

Fig. 31

Table 13 Icons for INS Recharge Progress Line

| Name | File | Icon | Size | Coordinates |
|---|---|---|---|---|
| Wait Signal | Wait_signal |  | 75w x 22h | R20 C10 |
| Recharging Antenna | recharge_antenna |  | 31w x 20h | R21 C7 |
| Recharging Sprites | energy_symbol |  | 11w x 11h | R25 C40 |
| INS Charging 0 to 25% | ins_charge_0_to_25 |  | 36w x 24h | R20 C53 |
| INS Charging 25 to 50% | ins_charge_25_to_50 |  | 36w x 24h | R20 C53 |
| INS Charging 50 to 75% | ins_charge_50_to_75 |  | 36w x 24h | R20 C53 |
| INS Charging 75 to 100% | ins_charge_75_to_100 |  | 36w x 24h | R20 C53 |
| INS Charging 0% | ins_charge_0 |  | 36w x 24h | R20 C53 |
| INS Charging 25% | ins_charge_25 |  | 36w x 24h | R20 C53 |
| INS Charging 50% | ins_charge_50 |  | 36w x 24h | R20 C53 |
| INS Charging 75% | ins_charge_75 |  | 36w x 24h | R20 C53 |
| INS Charging 100% | ins_charge_100 |  | 36w x 24h | R20 C53 |
| INS Recharge Complete | Msg_ins_charge_complete |  | 36w x 34h | R20 C30 |
| Antenna Too Hot | Msg_antenna_too_hot |  | 56w x 36h | R20 C20 |

Fig. 32

Table 14 Icons for INS Recharge Efficiency Line

| Name | File | Icon | Size | Coordinates |
|---|---|---|---|---|
| Recharge Efficiency-0 | recharge_efficiency_0 | ▭▭▭▭▭▭▭▭ | 65w x 9h | R46 C15 |
| Recharge Efficiency-1 | recharge_efficiency_1 | ■▭▭▭▭▭▭▭ | 65w x 9h | R46 C15 |
| Recharge Efficiency-2 | recharge_efficiency_2 | ■■▭▭▭▭▭▭ | 65w x 9h | R46 C15 |
| Recharge Efficiency-3 | recharge_efficiency_3 | ■■■▭▭▭▭▭ | 65w x 9h | R46 C15 |
| Recharge Efficiency-4 | recharge_efficiency_4 | ■■■■▭▭▭▭ | 65w x 9h | R46 C15 |
| Recharge Efficiency-5 | recharge_efficiency_5 | ■■■■■▭▭▭ | 65w x 9h | R46 C15 |
| Recharge Efficiency-6 | recharge_efficiency_6 | ■■■■■■▭▭ | 65w x 9h | R46 C15 |
| Recharge Efficiency-7 | recharge_efficiency_7 | ■■■■■■■▭ | 65w x 9h | R46 C15 |
| Recharge Efficiency-8 | recharge_efficiency_8 | ■■■■■■■■ | 65w x 9h | R46 C15 |

Fig. 33

Table 15 Icons for INSR Charge Status Screen

| Name | File | Icon | Size | Coordinates |
|---|---|---|---|---|
| Therapy On | status_stim_on | | 16w x 16h | R1 C6 |
| Therapy Off | status_stim_off | | 16w x 16h | R1 C6 |
| Audio On | status_beep_on | | 17w x 14h | R3 C27 |
| Audio Off | status_beep_off | | 17w x 14h | R3 C27 |
| INSR Charging 0 to 25% | Insr_charge_0_to_25 | | 36w x 26h | R24 C10 |
| INSR Charging 25 to 50% | Insr_charge_25_to_50 | | 36w x 26h | R24 C10 |
| INSR Charging 50 to 75% | Insr_charge_50_to_75 | | 36w x 26h | R24 C10 |
| INSR Charging 75 to 100% | Insr_charge_75_to_100 | | 36w x 26h | R24 C10 |
| INSR Charging 0% | Insr_charge_0 | | 36w x 26h | R24 C10 |
| INSR Charging 25% | Insr_charge_25 | | 36w x 26h | R24 C10 |
| INSR Charging 50% | Insr_charge_50 | | 36w x 26h | R24 C10 |
| INSR Charging 75% | Insr_charge_75 | | 36w x 26h | R24 C10 |
| INSR Charging 100% | Insr_charge_100 | | 36w x 26h | R24 C10 |
| Recharging Sprites | energy_symbol | | 11w x 11h | R37 C48 |
| INSR Plug | Insr_plug | | 29w x 23h | R26 C57 |

Fig. 34

Table 16 Icons for Information Messages

| Name | File | Icon | Size | Coordinates |
|---|---|---|---|---|
| All information messages | msg_insr_information | | 17w x 17h | R3 C5 |
| Antenna Too Hot | msg_antenna_too_hot | | 56w x 36h | R20 C20 |
| INS Battery Low | msg_ins_battery_low | | 36w x 24h | R27 C30 |
| INS Recharge Interrupted | msg_ins_charge_interrupted | Note 1 | 36w x 24h | R27 C30 |
| INS Recharge Complete | msg_ins_charge_complete | | 36w x 34h | R18 C30 |
| INSR Battery Low | msg_insr_battery_low | | 36w x 26h | R26 C30 |
| INSR Recharge Interrupted | msg_insr_charge_interrupted | Note 2 | 36w x 26h | R26 C30 |
| INSR Recharge Complete | msg_insr_charge_complete | | 36w x 34h | R18 C30 |
| Call Your Doctor – ERI | msg_call_your_doctor | | 57w x 43h | R8 C19 |
| IR Communication | msg_ir_communication; Note 3 | | 22w x 43h | R11 C37 |
| Text for Splash | Med 15pt font Note 4 | -- | -- | R14, C23 |
| Wait Signal – Splash | msg_wait_signal Note 4 | | 14w x 16h | R28 C41 |
| Connect INSR Antenna | msg_connect_insr_antenna | | 68w x 26h | R25 C14 |

Fig. 35

Table 17 Icons for Warning Messages and Physician Recharge Mode

| Name | File (*.bmp) | Icon | Size | Coordinates |
|---|---|---|---|---|
| All warning messages | msg_insr_attention |  | 16w x 14h | R4 C5 |
| Reposition Antenna | msg_reposition_antenna |  | 47w x 27h | R25 C6 |
| Reposition Antenna – Stim | msg_reposition_antenna_stim |  | 47w x 27h | R25 C6 |
| Press Start Charge | msg_press_test |  | 36w x 29h | R23 C54 |
| Press Therapy Off | msg_press_stim_off |  | 36w x 29h | R23 C54 |
| Press Therapy On | msg_press_stim_on |  | 36w x 29h | R23 C54 |
| Recharge Stimulator | msg_recharge_stim |  | 82w x 24h | R26 C7 |
| Recharge INSR | msg_recharge_insr |  | 76w x 26h | R25 C10 |
| Call Your Doctor | msg_call_your_doctor |  | 57w x 43h | R8 C19 |
| Physician Recharge[1] | msg_phys_recharge |  | 61w x 26h | R7 C17 |
| Physician Recharge – Antenna Too Hot[2] | msg_antenna_too_hot |  | 56w x 36h | R2 C20 |
| Values for Minutes/Seconds | Med18pt font | -- | -- | R40 C[3] |
| System Info | system_info[4] |  | 19w x 19h | R3 C5 |
| System Info Values | system font[5] | -- | -- | -- |

Fig. 36

| Name | Label | Function |
|---|---|---|
| Start Charge | ◆ | - Start charge<br>- Turn display on if pressed when recharger is powered down |
| Stop Charge | ✕ | - Stop charge |
| Audio | 🔊 | - Toggle audio on/off<br>- Turn display on if pressed when recharger is powered down |
| Therapy On | ⚡ | - Turn therapy on<br>- Turn display on if pressed when recharger is powered down |
| Therapy Off | ⭘ | - Turn therapy off<br>- Turn display on if pressed when recharger is powered down |

Fig. 37

EXTERNAL ENERGY TRANSFER SYSTEM FOR AN IMPLANTABLE MEDICAL DEVICE AND METHOD THEREFOR

RELATED APPLICATIONS

This application is claims priority to U.S. patent application Ser. No. 13/687,560, now U.S. Pat. No. 9,259,584, which is a divisional application of U.S. patent Ser. No. 10/958,191, now U.S. Pat. No. 8,346,361, which claims priority to U.S. Provisional Application Ser. No. 60/508,198, filed Oct. 2, 2003, entitled User Interface for External Charger for Implantable Medical Device, and also claims priority to U.S. Provisional Application Ser. No. 60/513,732, filed Oct. 23, 2003, entitled User Interface for External Charger for Implantable Medical Device. The entire contents of all of the foregoing applications are hereby incorporated by reference.

FIELD OF THE INVENTION

This invention relates to implantable medical devices and, in particular, to energy transfer devices, systems and methods for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function whether it be driving an electrical infusion pump, providing an electrical neurostimulation pulse or providing an electrical cardiac stimulation pulse. This electrical power is derived from a power source.

Typically, a power source for an implantable medical device can take one of two forms. The first form utilizes an external power source that transcutaneously delivers energy via wires or radio frequency energy. Having electrical wires which perforate the skin is disadvantageous due, in part, to the risk of infection. Further, continuously coupling patients to an external power for therapy is, at least, a large inconvenience. The second form utilizes single cell batteries as the source of energy of the implantable medical device. This can be effective for low power applications, such as pacing devices. However, such single cell batteries usually do not supply the lasting power required to perform new therapies in newer implantable medical devices. In some cases, such as an implantable artificial heart, a single cell battery might last the patient only a few hours. In other, less extreme cases, a single cell unit might expel all or nearly all of its energy in less than a year. This is not desirable due to the need to explant and re-implant the implantable medical device or a portion of the device. One solution is for electrical power to be transcutaneously transferred through the use of inductive coupling. Such electrical power or energy can optionally be stored in a rechargeable battery. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin.

Transcutaneous energy transfer through the use of inductive coupling involves the placement of two coils positioned in close proximity to each other on opposite sides of the cutaneous boundary. The internal coil, or secondary coil, is part of or otherwise electrically associated with the implanted medical device. The external coil, or primary coil, is associated with the external power source or external charger, or recharger. The primary coil is driven with an alternating current. A current is induced in the secondary coil through inductive coupling. This current can then be used to power the implanted medical device or to charge, or recharge, an internal power source, or a combination of the two.

Since it may be necessary for the patient to operate the external power source and since the patient may not be medically skilled nor electronically skilled, it is desirable that the external power source have a user interface that is both intuitive and simple to use and operate.

SUMMARY OF THE INVENTION

In an embodiment, the present invention provides an implantable medical device system. An implantable medical device provides a therapeutic output to a patient. An external patient control unit can be operatively coupled via telemetry with the implantable medical device allowing the patient to control the therapeutic output of the implantable medical device. An external energy transfer unit can be operatively coupled to the implantable medical device to transcutaneously transfer energy to the implantable medical device. The external patient control unit has a user interface operable by the patient having patient controls and display icons indicative of a status of operation of the patient control unit. The energy transfer unit has a user interface operable by the patient having patient controls and display icons indicative of a status of operation of the energy transfer unit. At least some of the patient controls and the display icons of the energy transfer unit are common with at least some of the patient controls and the display icons of the patient control unit.

In another embodiment, the present invention provides an external energy transfer unit adapted to transcutaneously transfer energy to an implantable medical device for providing a therapeutic output to a patient. The implantable medical device is capable of communication with an external patient control unit allowing the patient to control the therapeutic output of the implantable medical device. The external patient control unit has a user interface operable by the patient having patient controls and display icons indicative of a status of operation of the patient control unit. A user interface operable by the patient has patient controls and display icons indicative of a status of operation of the energy transfer unit. At least some of the patient controls and the display icons of the energy transfer unit are common with at least some of the patient controls and the display icons of the patient control unit.

In another embodiment, the present invention provides a method of providing therapeutic output to a patient using an implantable medical device. An external patient control unit is operatively coupled via telemetry with the implantable medical device allowing the patient to control the therapeutic output of the implantable medical device. An external energy transfer unit is operatively coupled to the implantable medical device to transcutaneously transfer energy to the implantable medical device. The external patient control unit has a user interface operable by the patient having patient controls and display icons indicative of a status of operation of the patient control unit. The energy transfer unit has a user interface operable by the patient and has patient controls and display icons indicative of a status of operation of the energy transfer unit. At least some of the patient controls and the display icons of the energy transfer unit are common with at least some of the patient controls and the display icons of the patient control unit.

In a preferred embodiment, at least one of the display icons is an icon representative of a state of charging of an energy storage device in the implantable medical device.

In a preferred embodiment, at least one of the patient controls is a control for adjusting the therapeutic output of the implantable medical device.

In a preferred embodiment, the external energy transfer unit inductively couples energy to the implantable medical device.

In a preferred embodiment, the implantable medical device has a rechargeable energy storage device and wherein the energy transfer unit charges the rechargeable energy storage device.

In another embodiment, the present invention provides an implantable medical device system. An implantable medical device provides a therapeutic output to a patient. An external energy transfer unit can be operatively coupled to transcutaneously transfer energy to the implantable medical device. The energy transfer unit is operable by the patient with less than three operative controls to control energy transfer from the external energy transfer unit to the implantable medical device.

In another embodiment, the present invention provides an external energy transfer unit adapted to transcutaneously transfer energy to an implantable medical device for providing a therapeutic output to a patient. Energy transfer circuitry transcutaneously transfers energy to the implantable medical device. Less than three operative controls control energy transfer from the external energy transfer unit to the implantable medical device.

In another embodiment, the present invention provides a method providing a therapeutic output to a patient with an implantable medical device. An external energy transfer unit is operatively coupled with the implantable medical device to transcutaneously transfer energy to the implantable medical device. The energy transfer unit is controlled with less than three operative controls to control energy transfer from the external energy transfer unit to the implantable medical device.

In a preferred embodiment, the energy transfer unit is operable with two operative controls to control energy transfer from the external energy transfer unit to the implantable medical device.

In a preferred embodiment, the two operative controls comprise a start control and a stop control.

In a preferred embodiment, the start control is a start button and wherein the stop control is a stop button.

In a preferred embodiment, the energy transfer unit also has operative controls to start and stop the therapeutic output of the implantable medical device.

In a preferred embodiment, the energy transfer unit also has a control to enable and silence audio feedback from the energy transfer unit.

In a preferred embodiment, the external energy transfer unit inductively couples energy to the implantable medical device.

In a preferred embodiment, the implantable medical device has a rechargeable energy storage device and wherein the energy transfer unit charges the rechargeable energy storage device.

In another embodiment, the present invention provides an implantable medical device system. An implantable medical device provides a therapeutic output to a patient. The implantable medical device is capable of receiving inductively coupled energy with a secondary coil and is capable of being transcutaneously controlled using an internal telemetry coil. An external antenna has a primary coil adapted to inductively transfer energy to the secondary coil of the implantable medical device when the external antenna is externally placed in proximity of the secondary coil. An external energy transfer unit is adapted to be operatively coupled by a cord to the external antenna driving the primary coil to inductively transfer energy to the implantable medical device. The energy transfer unit has an external telemetry coil allowing the energy transfer unit to communicate with the implantable medical device through the internal telemetry coil in order to at least partially control the therapeutic output of the implantable medical device.

In another embodiment, the present invention provides an external energy transfer system adapted to transcutaneously transfer energy to an implantable medical device for providing a therapeutic output to a patient. The implantable medical device is capable of receiving inductively coupled energy with a secondary coil and is capable of being transcutaneously controlled using an internal telemetry coil. An external antenna has a primary coil adapted to inductively transfer energy to the secondary coil of the implantable medical device when the external antenna is externally placed in proximity of the secondary coil. An external energy transfer unit is adapted to be operatively coupled by a cord to the external antenna driving the primary coil to inductively transfer energy to the implantable medical device. The energy transfer unit has an external telemetry coil allowing the energy transfer unit to communicate with the implantable medical device through the internal telemetry coil in order to at least partially control the therapeutic output of the implantable medical device.

In another embodiment, the present invention provides a method of controlling an implantable medical device for providing a therapeutic output. The implantable medical device is capable of receiving inductively coupled energy with a secondary coil and is capable of being transcutaneously controlled using an internal telemetry coil. Energy is inductively transferred to the secondary coil with an external antenna having a primary coil when the external antenna is externally placed in proximity of the secondary coil. The primary coil is driven with an external energy transfer unit operatively coupled by a cord to the external antenna to inductively transfer energy to the implantable medical device. An external telemetry coil in the energy transfer unit communicates with the implantable medical device through the internal telemetry coil in order to at least partially control the therapeutic output of the implantable medical device.

In a preferred embodiment, the inductively transferring step and the communicating step occur simultaneously.

In a preferred embodiment, the energy transfer unit can control the implantable medical device to turn the therapeutic output on and off.

In a preferred embodiment, the energy transfer unit can control the implantable medical device using the external telemetry coil while transferring energy to the implantable medical using the primary coil of the antenna.

In a preferred embodiment, the implantable medical device has a rechargeable energy storage device and wherein the energy transfer unit charges the rechargeable energy storage device.

BRIEF DESCRIPTION OF THE DRAWINGS

FIG. 5 illustrates a therapy status screen of an external programmer;

FIG. 6 illustrates access to menu selection of an external programmer;

FIG. 7 illustrate group selections of an external programmer;

FIG. 8 illustrate parameter selections of an external programmer;

FIG. 9A illustrate screens of an external programmer;

FIG. 9B illustrate messages of an external programmer;

FIG. 9C illustrate warnings of an external programmer;

FIG. 10 illustrate menu selections of an external programmer;

FIG. 11 illustrates audio status of an external programmer;

FIG. 12 illustrates contrast of an external programmer;

FIG. 13 illustrates INS/ENS time of an external programmer;

FIG. 14 illustrate time/number formats of an external programmer;

FIG. 15 illustrate patient programmer information;

FIG. 16 illustrates INS/ENS information;

FIG. 16A illustrates Telemetry N information;

FIG. 19 illustrates screen shots of charge status of an external charger;

FIG. 20 illustrates status messages displayed during charging of the INS;

FIG. 21 illustrates external power source charge status screens;

FIG. 22 illustrates status messages displayed during recharging of the external power source; and FIGS. 23A and 23B illustrate screens, information messages and warnings.

FIG. 24 shows a table of user interface components.

FIGS. 25-30 show tables of external programming unit user interface icons.

FIGS. 31-36 show tables of external charging unit user interface icons.

FIG. 37 shows a table of keypad buttons.

DETAILED DESCRIPTION OF THE INVENTION

Figure 1:
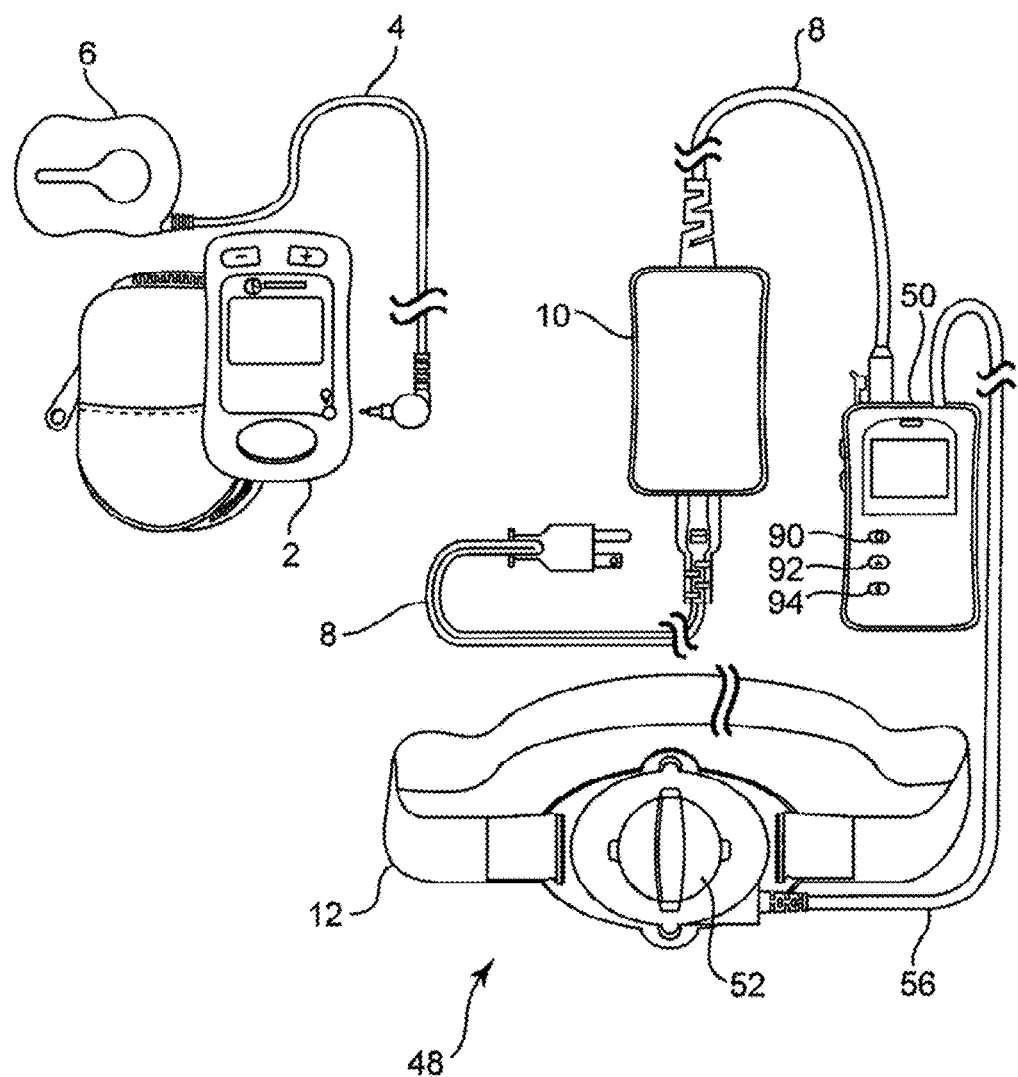
FIG. 1 is a block diagram of an external programmer and an external charging device for an implantable medical device such as can be utilized in the present invention.

In FIG. 1, external programming unit 2 is attachable via cord 4 to an external telemetry coil 6. External programming unit 2 can program operations implantable medical device 16 (FIG. 2) in a conventional manner using external telemetry coil 6. External antenna 52 is attachable via cord 56 to external charging device 48 is inductively transfer power to implantable medical device 16 when external antenna 52 is placed in proximity of a secondary coil 24 associated with implantable medical device 16. External charging device 48 receives AC power from cord 8 through transformer 10. External antenna 52 can be held in position on a patient with belt 12.

Figure 2:
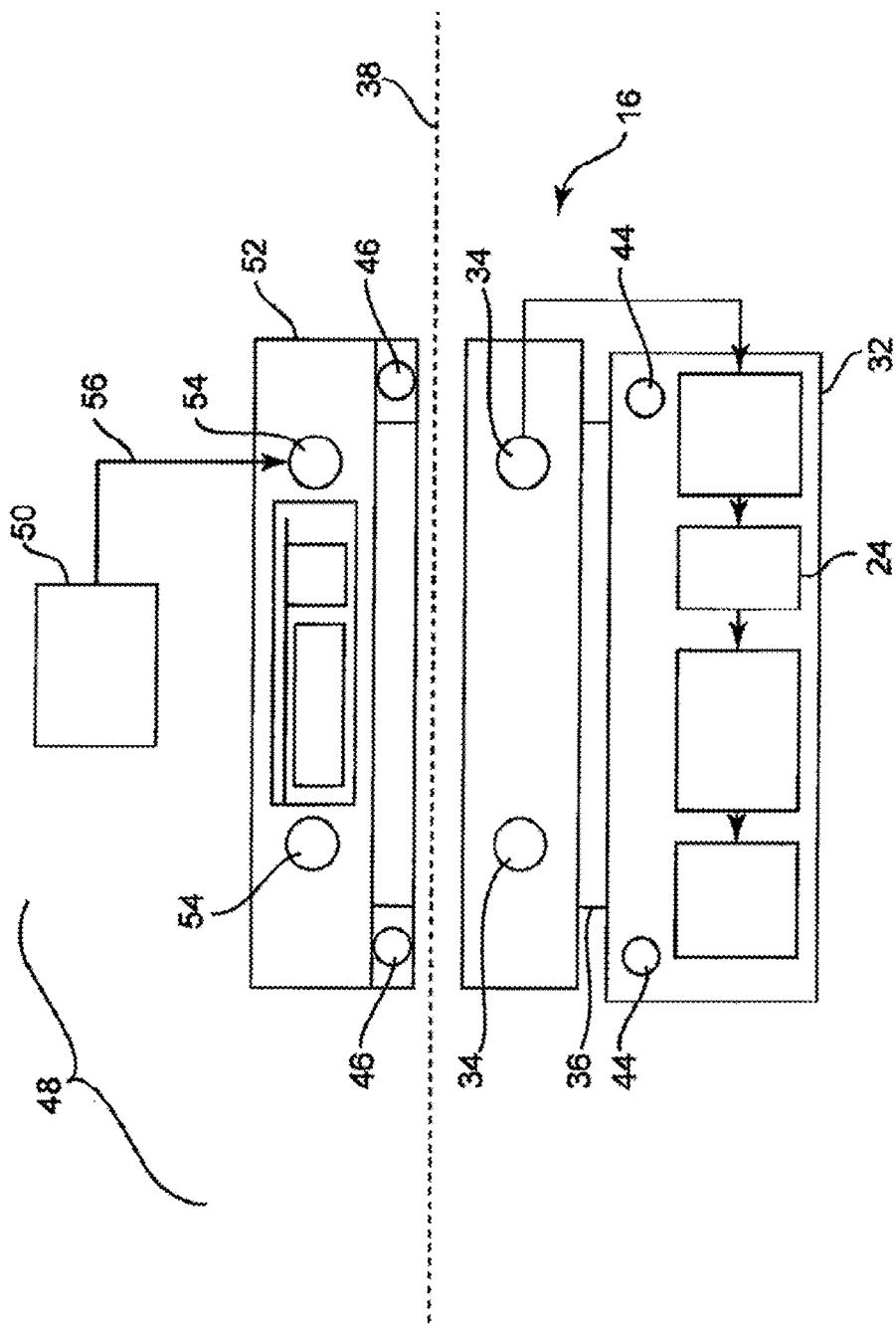
FIG. 2 is a detailed block diagram of an implantable medical device implanted sub-cutaneously and an associated external charging device in accordance with an embodiment of the present invention.
Figure 3:
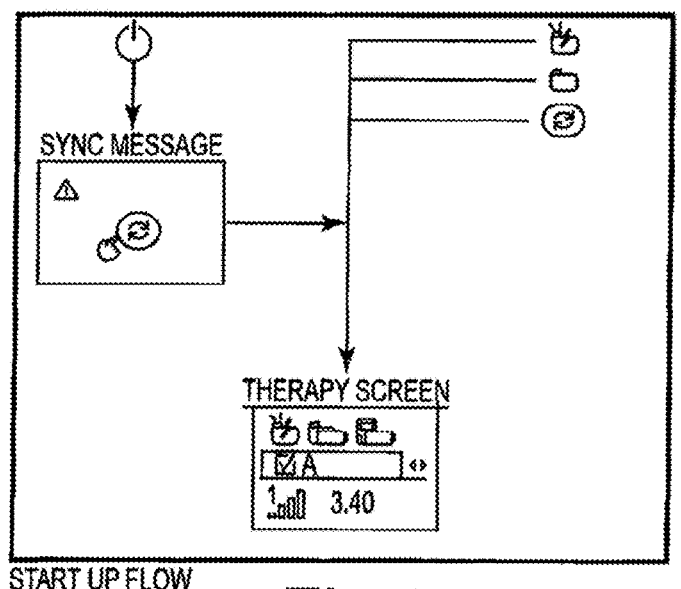
FIG. 3 illustrates the start-up flow of an external programmer usable in conjunction with an implantable medical device.
Figure 4:
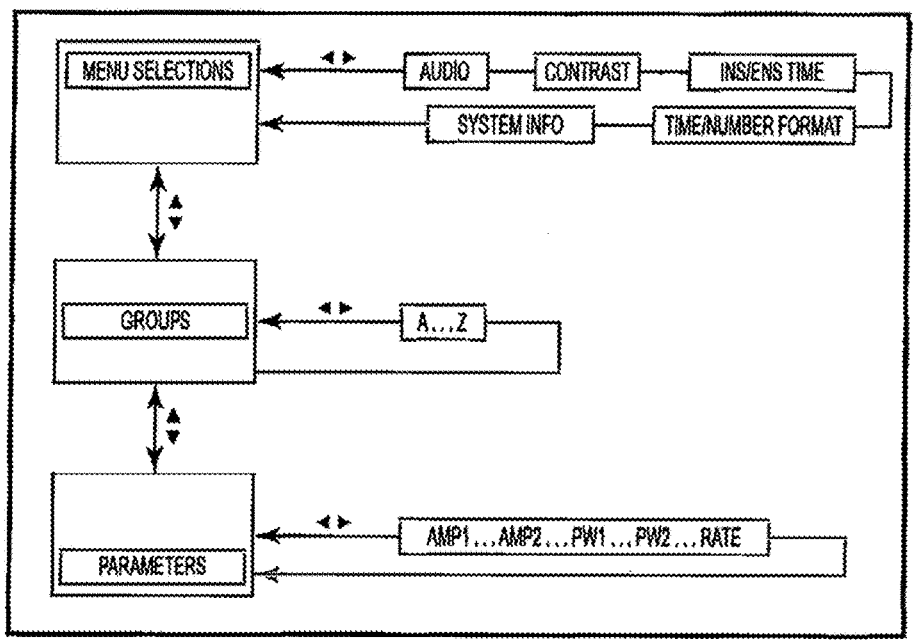
FIG. 4 illustrates operation flow of an external programmer usable in conjunction with an implantable medical device.

FIG. 2 illustrates an embodiment of implantable medical device 16 situated under cutaneous boundary 38. Charging regulation and therapy control is conventional. Implantable medical device 16 also has internal telemetry coil 44 configured in conventional manner to communicate through external telemetry coil 46 to an external programming device 2, charging unit 50 or other device in a conventional manner in order to both program and control implantable medical device and to externally obtain information from implantable medical device 16 once implantable medical device has been implanted. Internal telemetry coil 44, rectangular in shape with dimensions of 1.85 inches (4.7 centimeters) by 1.89 inches (4.8 centimeters) constructed from 150 turns of 43 AWG wire, is sized to be larger than the diameter of secondary charging coil 34. Secondary coil 34 is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 36 is positioned between secondary charging coil 34 and housing 32 and sized to cover the footprint of secondary charging coil 34.

Internal telemetry coil 44, having a larger diameter than secondary coil 34, is not completely covered by magnetic shield 36 allowing implantable medical device 16 to communicate with the external programming device with internal telemetry coil 44 in spite of the presence of magnetic shield 36.

Rechargeable power source 24 can be charged while implantable medical device 16 is in place in a patient through the use of external charging device 48. In a preferred embodiment, external charging device 48 consists of charging unit 50 and external antenna 52. Charging unit 50 contains the electronics necessary to drive primary coil 54 with an oscillating current in order to induce current in secondary coil 34 when primary coil 54 is placed in the proximity of secondary coil 34. Charging unit 50 is operatively coupled to primary coil by cable 56. In an alternative embodiment, charging unit 50 and antenna 52 may be combined into a single unit. Antenna 52 also contains external telemetry coil 46 which may be operatively coupled to charging unit 50 if it is desired to communicate to or from implantable medical device 16 with external charging device 48. Alternatively, antenna 52 may contain external telemetry coil 46 which can be operatively coupled to external programming device 2, either individually or together with external charging unit 48.

The user interface of external programming unit 2 is illustrated by reference to FIG. 3 through FIG. 16. The following terms are used throughout the description of the user interface of external programming unit 2.

As noted below in the explanation of acronyms utilized in the following paragraphs and table, DTC refers to desktop charger which is used to denote the AC power supply (transformer 10) and power cord (cord 8). The DTC is "docked" when external charger 48 is connected to an source of AC power. The DTC is "undocked" when external charger 48 is disconnected from a source of AC power.

DTC Desktop Charger
ENS External Neurostimulator
INS Implanted Neurostimulator
INSR Another name for the RX1 Patient Recharger. Acronym stands for Implanted Neurostimulator Recharger
LCD Liquid Crystal Display Refer to FIG. 3 and FIG. 4 for start-up flow and navigation flow, respectively.

User interface components in the keypad are shown in FIG. 24.

The LCD is backlit and consists of 96 (Horizontal)×58 (Vertical) dots with asymmetrical dots 0.35 (H)×0.4 (V). The active area on the LCD is 33.3 mm (H)×23.2 mm (V). Four colors of display available. These are named below (from lightest to darkest):
White
Light Gray
Dark Gray
Black Icons are shown in Tables 1-6 shown in FIGS. 25-30.
Notes:
Coordinates specified in the Tables 1-6 below are based on rows numbered 0-57 and columns numbered 0-95
Effective display area: rows 1-56, columns 1-94; always leave rows 0 and 57, columns 0 and 95 blank
With the exception of status_stim_on, status_stim_off and status_ins_battery_* in Table 1, check_off in Table 2, specified size in Tables 1-6 includes a 1-pixel wide white border around all symbols Notes
a) Column position will vary, depending on parameter value
b) All numbers will be displayed in R37; column position will vary, depending on parameter symbol and value
Note: display msg_wait_signal and msg_ir_communication for IR Communication Screen
Note: display Text for Splash (Med 15 pt font) and Wait Signal-Splash (msg_wait_signal) for Splash Screen
Note: column position will vary, depending on codes displayed Notes
1) Displayed on all menu selection screens
2) Row position will vary, depending on menu box that is displayed: R10 for menu_box_26×78; R34 for menu_box_16×78; R35 for menu_box_16×21 and menu_box_16×13; R40 for menu_box_27×78
3) C2 for hours; C27 for minutes
4) Column position will vary, depending on contrast setting
5) Column position will vary, depending on values
6) Display "PI" next to menu_info for Patient Programmer Information, "NSI" next to menu_info for INS/ENS Information and "TNI" next to menu_info for Telemetry N Information
7) Med15 pt font will be used for Patient Programmer Information and INS/ENS Information Therapy status screen display layout is divided vertically into three lines of information: status line, groups line and parameters line as shown in FIG. 5. When a successful initial interrogation has been performed, software will display the Therapy Status Screen of the active set with the following highlighting priority: parameters line if displayed; groups line if displayed; and status line.

Scroll up and scroll down keys will be used to access the status line, groups line and parameters line on the display. A box highlights user selection. Scroll left and right will be used to cycle through available choices for a selected line. Software will display a "real-time" INS charge level on the status line. The charge level will be updated and displayed whenever a parameter adjustment is made. Software will display programmer battery status on the status line.

Access to Menu Selections is from the status line are shown in FIG. 6. Initial interrogation will include data on all groups currently available to the patient ("Baseline" setting). Software will display labels for all groups the user can activate, including those containing no adjustable parameters. Refer to FIG. 7 for Group Selections. All unnecessary text will be removed from the display: e.g., if there is only 1 group, software will not display the groups line. Software will not display parameters that the user cannot adjust: i.e., the clinician programmer disallows access or upper and lower limits are the same. The user will access all available groups by scrolling through a linear list: A, B, C, . . . , Z. When the user scrolls to a different group, software will display the first adjustable parameter in the group. The user will scroll left/right through available groups to access an inactive group.

Software will display all adjustable parameters for inactive groups. The user will scroll down to highlight parameters and scroll left or right to view them. If a user presses Therapy Off or Therapy On when the screen displays an inactive group, software will turn the INS off, and display the Therapy Status Screen with the active group highlighted. A check in its check box will be used to indicate an active group (check_on); a check box without a check will be used to indicate inactive groups (check_off). The user will press the Sync key to activate a group at the displayed parameter value(s).

The neurostimulator does not have to be on to activate a new group. The user can activate a group when therapy is off. The user can activate a new group when the groups line is highlighted or when the parameters line is highlighted. The check box will be updated whenever a new group is activated.

Software will display labels for all parameters the user can adjust as shown in FIG. 8, Parameter Selections. Software will display the first adjustable parameter of the active group when a Sync has been performed for an initial interrogation. The user will access all adjustable parameters by scrolling through a linear list. The order of scrolling through adjustable parameters in a group is Amp1, Amp2, Amp3, Amp4, PW1, PW2, PW3, PW4, Rate, Amp1, . . . . Refer to FIG. 8, Parameter Selections. Increase/decrease keys will be inactive until a session has been initiated—i.e., the INS has been interrogated. When the user presses and holds the increase/decrease keys, software will send a change to the neurostimulator every ½ second. When the user changes a parameter, software will display the updated parameter value.

Therapy control events are described in screens, information messages and warnings that are displayed on the programmer as shown in FIGS. 9A, 9B and 9C. Operational requirements are described in tables that specify conditions for entry and expected changes in control.

Power Down Screen (Blank Display)
Screen Entry: User Control/System Event
System Timeout or Power Button Keypress

| User Control/ System Event | System Response: Table 10 reference |
|---|---|
| Power button | Start Screen, 14, 15 |
| Therapy On | 1, 2, 3, 5, 6, 7, 8, 9, 11, 12, 13, 14, 15, 20, 23, 24 |
| Therapy Off | 1, 2, 3, 5, 6, 7, 8, 9, 11, 12, 13, 14, 15, 20, 23, 24 |
| Sync | 1, 2, 3, 5, 6, 7, 8, 9, 11, 12, 13, 14, 15, 20, 23, 24 |
| Scroll up/down/ Scroll left/right | Ignore |
| Increase/Decrease | Ignore |
| Replace programmer batteries | Splash Screen |

Start Screen
Screen Entry: User Control/System Event
Power Button

| User Control/ System Event | System Response: Table 10 reference |
|---|---|
| Therapy On | 1, 2, 5, 6, 7, 8, 9, 11, 12, 13, 14, 15, 20, 23, 24 |
| Therapy Off | 1, 2, 5, 6, 7, 8, 9, 11, 12, 13, 14, 15, 20, 23, 24 |
| Sync | 1, 2, 3, 5, 6, 7, 8, 9, 11, 12, 13, 14, 20, 23, 24 |
| Power button/ System timeout | Power Down Screen |
| Scroll up/down/ Scroll left/right | Ignore |

| User Control/ System Event | System Response: Table 10 reference |
|---|---|
| Increase/Decrease | Ignore |
| Increase + Decrease and hold for 2-3 seconds | 10 |

Therapy Status Screen
Screen Entry: User Control/System Event
Telemetry Success

| User Control/ System Event | System Response: Table 10 reference |
|---|---|
| Therapy On | 1, 2, 3, 4, 5, 6, 7, 8, 9, 11, 12, 13, 14, 15, 20, 23, 24 |
| Therapy Off | 1, 2, 3, 4, 5, 6, 7, 8, 9, 11, 12, 13, 14, 15, 20, 23, 24 |
| Sync | 1, 2, 3, 4, 5, 6, 7, 8, 9, 11, 12, 13, 14, 15, 20, 23, 24 |
| Increase | 1, 2, 3, 4, 5, 6, 7, 8, 9, 11, 12, 13, 14, 15, 17, 18, 19, 20, 23, 24 |
| Decrease | 1, 2, 3, 4, 5, 6, 7, 8, 9, 11, 12, 13, 14, 15, 16, 19, 20, 23, 24 |
| Scroll left/right from status line | Audio Screen, Time/Number Formats |
| Power button/ System timeout | Power Down Screen |

The i symbol will be displayed on all information messages as shown in FIG. 9B. The user can clear all messages by pressing the 4-way button (Scroll up/down, Scroll left/right), Therapy Off to turn stimulation off or the Power button to turn the display off. If the system times out, the display will turn off (Power Down Screen). Refer to Table 7.

TABLE 1

Processing Requirements for Information Messages

| Message | User Control/System Response: Feedback/Next Screen |
|---|---|
| INS Battery Low | 4-way button: Therapy Status |
| | Stim Off: Table 10-1, 2, 3, 6, 11, 12, 13, 14, 15, 23, 24 |
| | Stim On: ignore |
| | Sync: ignore |
| | Increase/Decrease: ignore |
| | System timeout or Power button: Power Down |
| ENS Battery Low | 4-way button: Therapy Status |
| | Stim Off: Table 10-1, 2, 3, 8, 9, 12, 13, 14, 15, 20, 23, 24 |
| | Stim On: ignore |
| | Sync: ignore |
| | Increase/Decrease: ignore |
| | System timeout or Power button: Power Down |
| Programmer Battery Low | 4-way button: Previous screen |
| | Stim Off: Table 10-1, 2, 3, 5, 6, 7, 8, 9, 11, 12, 13, 15, 20, 23, 24 |
| | Stim On: ignore |
| | Sync: ignore |
| | Increase/Decrease: ignore |
| | System timeout or Power button: Power Down |
| Amp at Upper Limit | 4-way button: Therapy Status |
| | Stim Off: Table 10-1, 2, 3, 5, 6, 7, 8, 9, 11, 12, 13, 14, 15, 20, 23, 24 |
| | Stim On: ignore |
| | Sync: ignore |
| | Increase/Decrease: ignore |
| | System timeout or Power button: Power Down |
| PW at Upper Limit | 4-way button: Therapy Status |
| | Stim Off: Table 10-1, 2, 3, 5, 6, 7, 8, 9, 11, 12, 13, 14, 15, 20, 23, 24 |
| | Stim On: ignore |
| | Sync: ignore |
| | Increase/Decrease: ignore |
| | System timeout or Power button: Power Down |

TABLE 1-continued

Processing Requirements for Information Messages

| Message | User Control/System Response: Feedback/Next Screen |
|---|---|
| Rate at Upper Limit | 4-way button: Therapy Status<br>Stim Off: Table 10-1, 2, 3, 5, 6, 7, 8, 9, 11, 12, 13, 14, 15, 20, 23, 24<br>Stim On: ignore<br>Sync: ignore<br>Increase/Decrease: ignore<br>System timeout or Power button: Power Down |
| Amp at Lower Limit | 4-way button: Therapy Status<br>Stim Off: Table 10-1, 2, 3, 5, 6, 7, 8, 9, 11, 12, 13, 14, 15, 20, 23, 24<br>Stim On: ignore<br>Sync: ignore<br>Increase/Decrease: ignore<br>System timeout or Power button: Power Down |
| PW at Lower Limit | 4-way button: Therapy Status<br>Stim Off: Table 10-1, 2, 3, 5, 6, 7, 8, 9, 11, 12, 13, 14, 15, 20, 23, 24<br>Stim On: ignore<br>Sync: ignore<br>Increase/Decrease: ignore<br>System timeout or Power button: Power Down |
| Rate at Lower Limit | 4-way button: Therapy Status<br>Stim Off: Table 10-1, 2, 3, 5, 6, 7, 8, 9, 11, 12, 13, 14, 15, 20, 23, 24<br>Stim On: ignore<br>Sync: ignore<br>Increase/Decrease: ignore<br>System timeout or Power button: Power Down |
| Poor Communication-INS | Allow a repeat of the last keypress for Stim On, Sync, Increase and Decrease<br>4-way button: Sync Up Required<br>Stim Off: Table 10-1, 2, 3, 5, 6, 11, 12, 13, 14, 15<br>Stim On: Table 10-1, 2, 3, 5, 6, 11, 12, 13, 14, 15<br>Sync: Table 10-1, 2, 3, 5, 6, 11, 12, 13, 14, 15<br>Increase/Decrease: Table 10-1, 2, 3, 5, 6, 11, 12, 13, 14, 15, 16, 17, 18, 19<br>System timeout or Power button: Power Down |
| Poor Communication-ENS | Allow a repeat of the last keypress for Stim On, Sync, Increase and Decrease<br>4-way button: Sync Up Required<br>Stim Off: Table 10-2, 7, 8, 9, 12, 13, 14, 15, 20, 23, 24<br>Stim On: Table 10-2, 7, 8, 9, 12, 13, 14, 15, 20, 23, 24<br>Sync: Table 10-2, 7, 8, 9, 12, 13, 14, 15, 20, 23, 24<br>Increase/Decrease: Table 10-2, 7, 8, 9, 12, 13, 14, 15, 16, 17, 18, 19, 20, 23, 24<br>System timeout or Power button: Power Down |
| Sync Up | 4-way button: Therapy Status<br>Stim Off: Table 10-1, 2, 3, 5, 6, 7, 8, 9, 11, 12, 13, 14,15, 20, 23, 24<br>Stim On: Table 10-1, 2, 3, 5, 6, 7, 8, 9, 11, 12, 13, 14, 15, 20, 23, 24<br>Sync: Table 10-1, 2, 3, 5, 6, 7, 8, 9, 11, 12, 13, 14, 15,20<br>Increase/Decrease: ignore<br>System timeout or Power button: Power Down |
| Turn Stimulation On | 4-way button: Therapy Status<br>Stim Off: ignore<br>Stim On: Table 10-1, 2, 3, 5, 6, 7, 8, 9, 11, 12, 13, 14, 15, 20, 23, 24<br>Sync: ignore<br>Increase/Decrease: ignore<br>System timeout or Power button: Power Down |
| Connect ENS Cable | 4-way button: Sync Up Required<br>Stim Off: Table 10-2, 7, 8, 9, 12, 13, 14, 15, 20, 23, 24<br>Stim On: Table 10-2, 7, 8, 9, 12, 13, 14, 15, 20, 23, 24<br>Sync: ignore<br>Increase/Decrease: ignore<br>System timeout or Power button: Power Down |

The exclamation mark symbol will be displayed on all warnings as shown in FIG. 9C. All warnings will remain on the display until the user takes appropriate action. Refer to Table 8.

TABLE 2

Processing Requirements for Warning Messages

| Message | User Action/System Response: Feedback/Next Screen |
|---|---|
| Recharge Stimulator | System timeout or Power button: Power Down |
| Replace ENS Battery | System timeout or Power button: Power Down |
| Replace Programmer Battery | Replace programmer battery: Start Screen System timeout or Power button: Power Down |
| Sync Up Required | Sync button or Therapy On or Therapy Off: Therapy Status System timeout or Power button: Power Down |
| Call Your Doctor | Therapy Off and telemetry success with audio feedback: Call Your Doctor Therapy Off and telemetry failure with audio feedback: Call Your Doctor System timeout or Power button: Power Down |
| Call Your Doctor-EOS | System timeout or Power button: Power Down |
| Call Your Doctor-POR | System timeout or Power button: Power Down |

"In the box" messages are described in Table 9.

"In the Box" Messages

Software will notify the user with 3 beeps when "In the Box" messages are displayed All "In the Box" messages will remain on the display until the system times out or the user presses the Power button to turn off the display. Refer to Table 9.

TABLE 3

Processing Requirements for "In the Box" Messages

| Message | User Action/System Response: Feedback / Next Screen |
|---|---|
| INS in the Box | System timeout or Power button: Power Down |
| ENS in the Box | System timeout or Power button: Power Down |

Therapy control events are described in Table 10.

TABLE 4

Processing Requirements for Therapy Control Events and Device Communication

| User Control/System Event | System Response |
|---|---|
| 1. Communicating with the INS | Display Communicating-INS Message |
| 2. Successful telemetry | Display Therapy Status Screen |
| 3. Telemetry failure-INS | Display Poor Communication-INS Message |
| 4. Software is unable to refresh/update the Therapy Status Screen after a telemetry failure | Display Sync Up Required Warning |
| 5. INS battery low | Display INS Battery Low Message |
| 6. INS battery depleted | Display Recharge Stimulator Warning |
| 7. ENS battery low or battery disconnected | Display ENS Battery Low Message |
| 8. ENS battery depleted | Display Replace ENS Battery Warning |
| 9. ENS screening cable disconnected | Display Connect ENS Cable Message |
| 10. User presses Increase + Decrease and holds for 2-3 seconds | Display Patient Information Screen (Error! Reference source not found.) |
| 11. INS error-EOS | Display Call Your Doctor-EOS Warning |
| 12. INS error-battery voltage too high;/ENS error-POR, battery voltage too high | Display Call Your Doctor Warning |
| 13. System Error and Warning | Display Call Your Doctor Warning |
| 14. Patient programmer battery low | Display Programmer Battery Low Message |
| 15. Patient programmer battery depleted | Display Replace Programmer Battery Warning |
| 16. Parameter at lower limit | Display At Lower Limit Message |
| 17. Parameter at upper limit or out of reg | Display At Upper Limit Message |
| 18. Increase with therapy off | Display Turn Stimulation On Message |
| 19. Increase/decrease parameter of inactive group | Display Sync Up Message |
| 20. ENS error-POR, battery voltage too low | Display Communicating-ENS, followed by INS/ENS Time with 12:00 displayed |
| 21. Communicating via IR | Display IR Communication Screen |
| 22. Replace programmer batteries | Display Splash Screen |
| 23. Communicating with the ENS | DisplayCommunicating-ENS Message |
| 24. Telemetry failure-ENS | Display Poor Communication-ENS Message |
| 25. INS error-locked normal | Display INS in the Box Message |
| 26. ENS error-ENS has no programs or groups | Display ENS in the Box Message |
| 27. INS error-POR | Display Call Your Doctor -POR Warning |

Access to menu selections is from the status line on the Therapy Screen as shown in FIG. 10.

The display is divided vertically into two lines of information: menu option line and value line. Scroll up and down keys will be used to access the menu option line and the value line on the display. A box highlights user selection. Scroll right and left and increase/decrease keys will be used to change values for Audio, Contrast, Time/Number Format and the Information options. In addition, Increase/decrease keys will be used to change values.

Software will display screens for the menu options in Table 11 Menu Selections.

TABLE 5

Menu Selections and Navigation Flow

| Menu Item | References |
|---|---|
| Audio | FIG. 11, Table 12-1, 3, 9 |
| Contrast | FIG. 12, Table 12-1, 3, 4, 6, 7, 9 |
| INS/ENS Time | FIG. 13, Table 12-1, 2, 4, 7, 8, 9 |
| Time/Number Format | FIG. 14, Table 12-1, 3, 9 |
| Patient Programmer Information | FIG. 15, Table 12-1, 2, 9, 10 |
| INS/ENS Information | FIG. 16, Table 12-1, 2, 9, 10 |
| Telemetry N Information | FIG. 16A, Table 12-1, 2, 9, 10 |

The user interface of the external charger is described below. A description of the user interface for an external recharger for an implantable medical device is described. The appearance of the screens and how users interact with these screens are defined.

The following terms are used throughout the description of the user interface for the external charger.

DTC Desktop Charger

ENS External Neurostimulator

INS Implanted Neurostimulator

INSR Another name for the RX1 Patient Recharger. Acronym stands for Implanted Neurostimulator Recharger LCD Liquid Crystal Display Refer to FIG. 17 and FIG. 18 for navigation flow.

Figure 17:
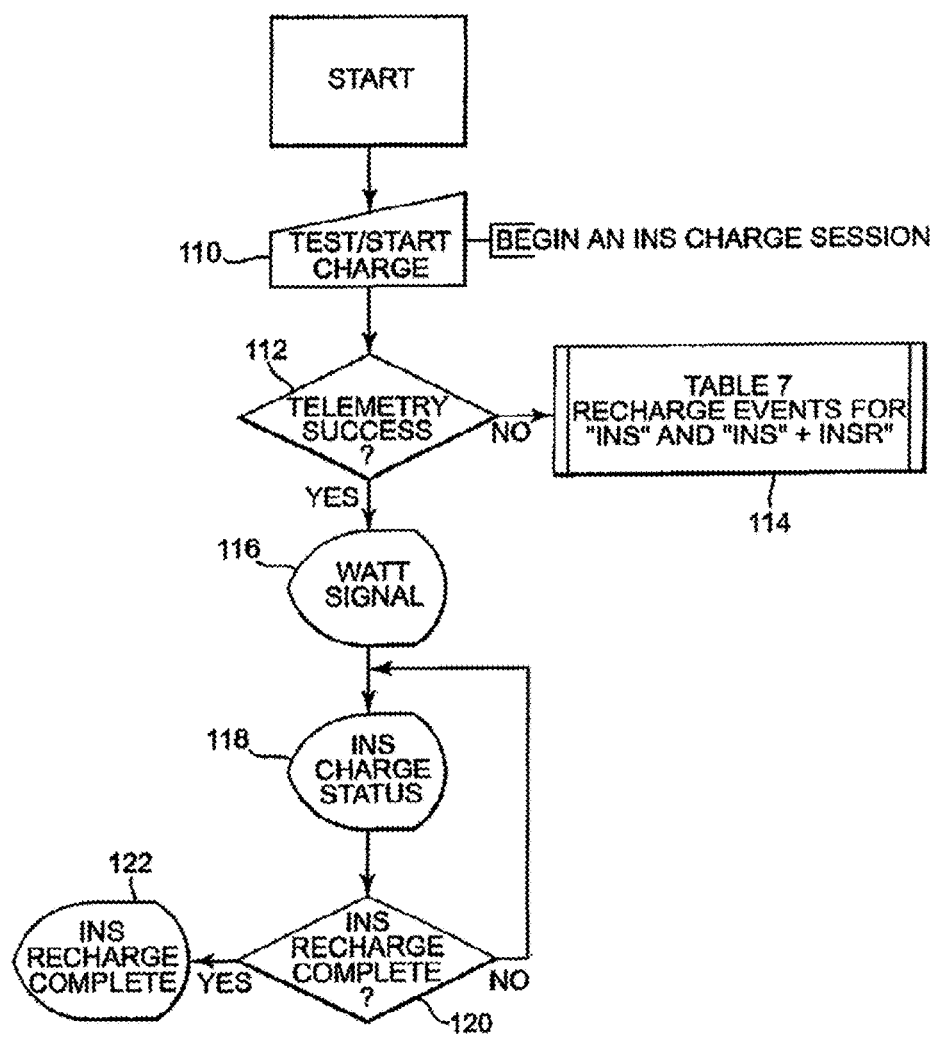
FIG. 17 illustrates the navigation flow of an external charger for recharging the INS.

FIG. 17 illustrates a process for charging rechargeable power source 24 in implantable medical device 16 by using external charging device 48.

In order to charge rechargeable power source 24, a patient may use belt 12 to attach external antenna 52 to the patient's body at approximately the location of implanted medical device 16. It is desirable that primary coil 54 of external antenna 52 be aligned as closely as possible with secondary coil 34 of implantable medical device 16. Techniques for attaching external antenna 52 to the patient's body and positioning primary coil 54 in close proximity to secondary coil 34 can be found in co-pending U.S. patent application Ser. No. 10/837,506, filed Apr. 30, 2004, the entire contents of which are hereby incorporated by reference. This application claims priority from U.S. Provisional Patent Application Ser. No. 60/508,174, filed Oct. 2, 2003.

After affixing external antenna 52 to the approximate location of implantable medical device 16, the patient (or other user such as a medical professional or family member assisting the patient) may then press (step 110) the "Start Charge" button 90 (FIG. 1) on charging unit 50.

Charging unit 50 then determines (step 112) if telemetry with implantable medical device 16 is successful. If telemetry is unsuccessful (step 114), an error message is generated such as a telemetry timeout (Reposition Antenna-Press Start Charge), system error (Antenna Too Hot) or external charging device 48 error due to INSR battery low or INSR battery depleted and external charging device displays the appropriate message. If telemetry is successful, then charging unit 50 waits (step 116) and the appropriate charge status may be indicated (step 118) in the display of charging unit 50.

If charging of rechargeable power source 24 is not yet complete (step 120), charging unit 50 returns through step 118. The surface temperature of antenna 52 is monitored as well as the charging current and battery voltage levels. An error message is generated and charging is suspended if measurements are not within limits.

Once charging of rechargeable power 24 is complete (step 122), charging unit 50 indicates in the display that charging is complete and the user may press the "Stop Charge" button 92 on charging unit 50 to terminate the charging process. Of course, it is to recognized and understood that the "Stop Charge" button 92 may be pressed at any time during the charging process in order to terminate the charging process, i.e., the user need not wait until the complete charging has been indicated.

Charging unit 50 may be operated to charge rechargeable power 24 in implantable medical device 16 by the use of only two buttons, namely the "Start Charge" button 90 and the "Stop Charge" button 92. These are the only two buttons which need be used. While a preferred embodiment of charging unit 50 does contain a third button, namely "Silence" button 94, this third button is not necessary. "Silence" button 94 is used only to disable, or to re-enable, audio output of charging unit 50. Since audio feedback is not required for the charging process, this button may be used or not at the convenience of the user.

In an alternative embodiment, charging unit 50 may itself be powered by a rechargeable power source, such as a battery. Since the charging process could take several hours, it would be desirable.

Figure 18:
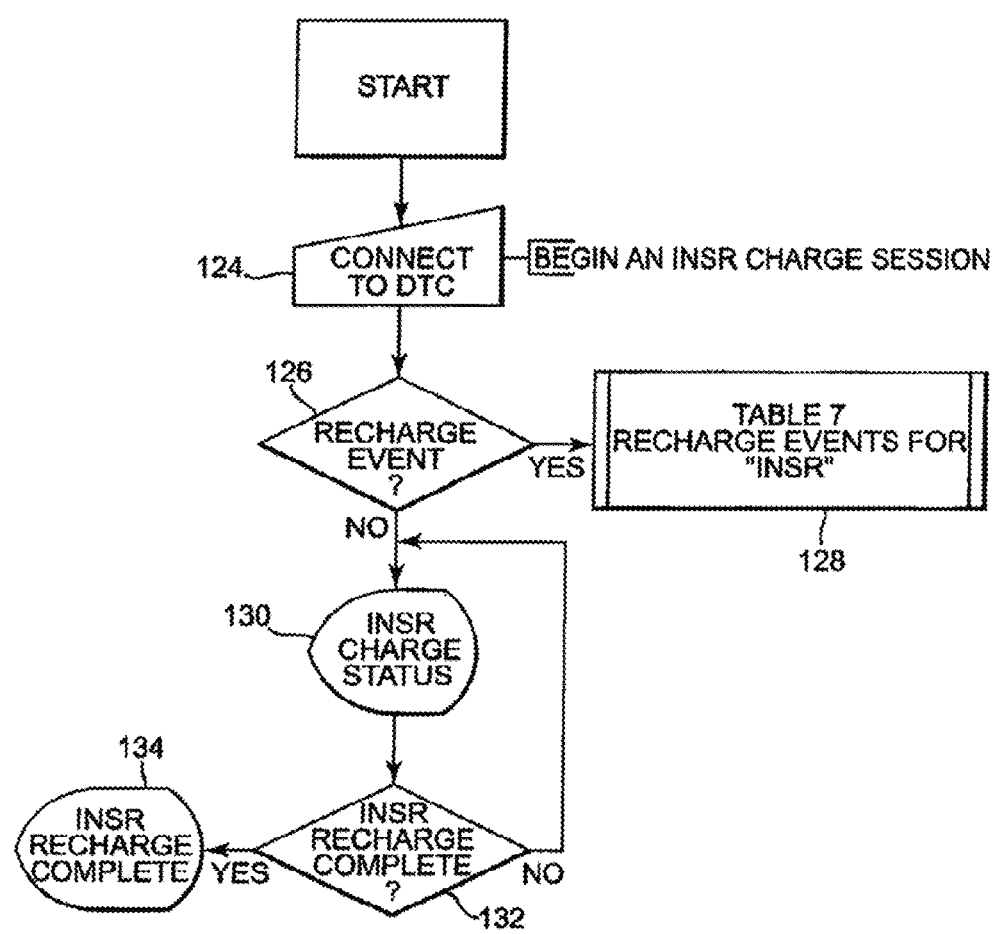
FIG. 18 illustrates the navigation flow of an external charger for recharging the external power source.

FIG. 18 illustrates the process used to charge the external charging unit 48. The external charging unit 48 is connected (step 124) to a suitable power source, such as a readily available AC power outlet. A check is made (step 126) to determine whether a "recharge event", i.e., an alert or alarm condition, has occurred and, if so, issue the appropriate message (step 128). If a "recharge event" has not occurred, the process updates and displays (step 130) the charge status of external charging device 48. If recharge of external charging is not complete (step 132), the process again updates and displays the charging status in step 130. Once charging of external charging device 48 is complete (step 134), charging unit 50 displays a message indicative of a complete charging process.

The LCD is backlit and consists of 96 (Horizontal)×58 (Vertical) dots with asymmetrical dots 0.35 (H)×0.4 (V). The active area on the LCD is 23.2 mm (V)×33.3 mm (H).

Four colors of display are available. These are named below (from lightest to darkest):

White

Light Gray

Dark Gray

Black

The keypad has the following buttons shown in FIG. 37.

See Tables 12 through 17 as shown in FIGS. 31-36 for icons.

Note 1: display INS battery status symbol for current charge level: ins_charge_25, ins_charge_50, ins_charge_75 (refer to Table 12), or msg_ins_charge_complete (refer to Table 15)

Note 2: display INSR battery status symbol for current charge level: insr_charge_25, insr_charge_50, insr_charge_75 (refer to Table 14)

Note 3: display msg_insr_wait_signal (refer to Table 11) and msg_ir_communication (refer to Table 5) for IR Communication Screen Note 4: display Text for Splash (Med 15 pt font) and Wait Signal—Splash (msg_wait_signal) for Splash Screen The INS charge status screen display is divided vertically into three lines of information: status line, recharge progress line and recharge efficiency line. Refer to FIG. 19 and FIG. 20.

Therapy On, Therapy Off, Start Charge and Stop Charge are dedicated function keys. When the display is blank and the user presses Therapy On, Therapy Off or Start Charge, software will perform the function and turn the display on. System timeout is <30 seconds.

The INS battery status display has 5 settings: 0%, 25%, 50%, 75% and 100%. During recharge, software will display the appropriate quartiles in solid fill and the next higher quartile in a flashing on/off manner every second. The exception is 100%. Even if the INS battery voltage indicates 100%, software will flash the last quartile until the recharge session is complete.

The INSR charge status screen display is divided vertically into two lines of information: status line and recharge progress line. Refer to FIG. 21, INSR Charge Status Screen, and FIG. 22, Recharging the INSR.

The INSR battery status has 5 settings: 0%, 25%, 50%, 75% and 100%. During recharge, software will display the appropriate quartiles in solid fill and the next higher quartile in a flashing on/off manner every second. The exception is 100%. Even if the INSR battery voltage indicates 100%, software will flash the last quartile until the recharge session is complete.

Figure 23B:

Recharging events are described in screens, information messages and warnings that are displayed on the recharger as shown in FIG. 23A and FIG. 23B. Operational requirements are described in tables that specify conditions for entry and expected changes in control. Refer to the operational requirements for each screen in this section.

The i symbol will be displayed on all information messages. With the exception of INSR System Information screen, the user can exit the messages by pressing Audio or wait for the system to timeout. Therapy On and Off will always be active when the messages are displayed. When the user presses Therapy On or Off, software will turn stimulation on/off and clear the information message.

The exclamation mark symbol will be displayed on all warnings. All warnings will remain on the display until the user takes appropriate action.

1—Power Down Screen (Blank Display)
Screen Entry: User Control/System Event
  System Timeout from Start Screen—not Docked

| User Control/ System Event | System Response: Feedback/Next Screen (requirement) |
|---|---|
| Therapy On/Off | Telemetry success: Start Screen-Not Docked with Therapy On/Off icon on status line (Table 17-22) |
| | Telemetry event: refer to Table 18 |
| Start Charge | Antenna temperature OK: Wait Screen (Table 17-1) |
| | Antenna too hot: Antenna Too Hot Message (Table 17-30) |
| | Antenna failure: Call Your Doctor Warning (Table 17-18) |
| | Antenna disconnected: Connect INSR Antenna Message (Table 17-14) |
| | INSR battery low: INSR Battery Low Message (Table 17-8) |
| | INSR battery depleted: Recharge INSR Warning (Table 17-9) |
| Stop Charge | No change |
| Audio | Start Screen-Not Docked (Table 17-24, 25) |
| | INSR battery low: INSR Battery Low Message (Table 17-8) |
| | INSR battery depleted: Recharge INSR Warning (Table 17-9) |
| Attach DTC | INSR recharge complete: INSR Recharge Complete Message (Table 17-11) |
| | INSR recharge incomplete: INSR Charge Status Screen (Table 17-7) |
| Audio + Stop Charge | INSR System Information Message (Table 17-17) |
| Audio + Start Charge and hold for > 10 seconds | Antenna temperature OK: Physician Recharge Screen (Table 17-21) |
| | Antenna too hot: Physician Recharge-Antenna Too Hot (Table 17-31) |

2—Start Screen—not Docked
Screen Entry: User Control/System Event
  Therapy On/Off keys when the recharger is powered down
  Audio key when the recharger is powered down
  Any key from Splash Screen
  Detach DTC
  System timeout or message clear when DTC is detached
  Stop Charge from Physician Recharge Screen or Physician Recharge—Antenna Too Hot Screen
  Host terminates the session, the Reset button is activated or the user presses Audio from IR Communication Screen

| User Control/ System Event | System Response: Feedback/Next Screen (requirement) |
|---|---|
| Therapy On/Off | Telemetry success: Therapy On/Off icon on status line (Table 17-22) |
| | Telemetry event: refer to Table 18 |
| Start Charge | Antenna temperature OK: Wait Screen (Table 17-1) |
| | Antenna too hot: Antenna Too Hot Message (Table 17-30) |
| | Antenna failure: Call Your Doctor Warning (Table 17-18) |
| | Antenna disconnected: Connect INSR Antenna Message (Table 17-14) |
| | INSR battery low: INSR Battery Low Message (Table 17-8) |
| | INSR battery depleted: Recharge INSR Warning (Table 17-9) |
| Stop Charge | No change |
| Audio | Audio icon (Table 17-24) |
| INSR battery low | INSR Battery Low Message (Table 17-8) |
| INSR battery depleted | Recharge INSR Warning (Table 17-9) |
| System error | Call Your Doctor Warning (Table 17-18) |
| Attach DTC | INSR recharge complete: INSR Recharge Complete Message (Table 17-11) |
| | INSR recharge incomplete: INSR Charge Status Screen (Table 17-7) |
| Audio + Stop Charge | INSR System Information Message (Table 17-17) |
| Audio + Start Charge and hold for > 10 seconds | Antenna temperature OK: Physician Recharge Screen (Table 17-21) |
| | Antenna too hot: Physician Recharge-Antenna Too Hot (Table 17-31) |
| System timeout | Power Down Screen |

3—Start Screen—Docked
Screen Entry: User Control/System Event
   System timeout or message clear
   Any key from Splash Screen
   Host terminates the session, the Reset button is activated or the user presses Audio from the Splash Screen
   Stop Charge from Physician Recharge Screen or Physician Recharge—Antenna Too Hot Screen

| User Control/ System Event | System Response: Feedback/Next Screen (requirement) |
|---|---|
| Therapy On/Off | Telemetry success: Therapy On/Off icon on status line (Table 17-22) |
| | Telemetry event: refer to Table 18 |
| Start Charge | Antenna temperature OK: Wait Screen (Table 17-1) |
| | Antenna too hot: Antenna Too Hot Message (Table 17-30) |
| | Antenna failure: Call Your Doctor Warning (Table 17-18) |
| | Antenna disconnected: Connect INSR Antenna (Table 17-14) |
| Stop Charge | No change |
| Audio | Audio icon (Table 17-24) |
| System error | Call Your Doctor Warning (Table 17-18) |
| Detach DTC | Start Screen-Not Docked |
| Audio + Stop Charge | INSR System Information Message (Table 17-17) |
| Audio + Start Charge and hold for > 10 seconds | Antenna temperature OK: Physician Recharge Screen (Table 17-21) |
| | Antenna too hot: Physician Recharge-Antenna Too Hot (Table 17-31) |

4—Wait Screen
Screen Entry: User Control/System Event
   Start Charge
   Antenna temperature OK
   System timeout or message clear

| User Control/ System Event | System Response: Feedback/Next Screen (requirement) |
|---|---|
| Therapy On/Off | No change |
| Telemetry success | INS Charge Status Screen or INS Charge Status-90 to 100% Screen (Table 17-2) |
| Telemetry failure or poor charging condition | Reposition Antenna-Press Start Charge Warning (Table 17-12) |
| INS error: ERI | Call Your Doctor-ERI Message (Table 17-19) |
| INS error: POR | Call Your Doctor-POR Message (Table 17-27) |
| INS error: EOS, battery-voltage too high | Call Your Doctor Warning (Table 17-18) |
| INSR battery low | INSR Battery Low Message (Table 17-8) |
| INSR battery depleted | Recharge INSR Warning (Table 17-9) |
| Antenna too hot | INS Charge Status-Antenna Too Hot (Table 17-13) |
| Antenna failure | Call Your Doctor Warning (Table 17-18) |
| Antenna disconnected | Connect INSR Antenna Message (Table 17-14) |
| System error | Call Your Doctor Warning (Table 17-18) |
| Start Charge | No change |
| Stop Charge (not docked) | Start Screen-Not Docked |
| Stop Charge (docked) | INSR recharge incomplete: INSR Charge Status Screen (Table 17-7) |
| | INSR recharge complete: INSR Recharge Complete Message (Table 17-11) |
| Audio | No change |
| Attach DTC | No change |
| Detach DTC | No change |
| Audio + Stop Charge | No change |
| Audio + Start Charge and hold for > 10 seconds | No change |

5—INS Charge Status Screen
Screen Entry: User Control/System Event
  Telemetry success
  System timeout or message clear
  Antenna temperature OK

| User Control/ System Event | System Response: Feedback/Next Screen (requirement) |
| --- | --- |
| Therapy On/Off | Telemetry success: Therapy On/Off icon on status line (Table 17-22) |
| | Telemetry event: refer to Table 18 |
| Start Charge | Antenna temperature OK: refresh recharge efficiency line (Table 17-26) |
| | Antenna too hot: INS Charge Status-Antenna Too Hot (Table 17-13) |
| Stop Charge | Charge complete: INS Recharge Complete Message (Table 17-6) |
| | Charge incomplete and not INS battery low: INS Recharge Interrupted Message (Table 17-5) |
| | INS battery low: INS Battery Low Message (Table 17-3) |
| | INS battery depleted: Recharge Stimulator Warning (Table 17-4) |
| Audio | Toggle Audio icon (Table 17-24) |
| Attach DTC | Power source symbol on status line (Table 17-23) |
| Detach DTC | INSR battery low: INSR Battery Low Message (Table 17-8) |
| | INSR battery depleted: Recharge INSR Warning (Table 17-9) |
| | Status line without power source symbol (Table 17-23) |
| INS recharge complete | INS Recharge Complete Message (Table 17-6) |
| INS error: ERI | Call Your Doctor ERI Message (Table 17-19) |
| INS error: POR | Call Your Doctor-POR Message (Table 17-27) |
| INS error: EOS, battery voltage too high | Call Your Doctor Warning (Table 17-18) |
| Antenna too hot | INS Charge Status-Antenna Too Hot (Table 17-13) |
| Antenna failure | Call Your Doctor Warning (Table 17-18) |
| Antenna disconnected | Connect INSR Antenna Message (Table 17-14) |
| INSR battery low | INSR Battery Low Message (Table 17-8) |
| INSR battery depleted | Recharge INSR Warning (Table 17-9) |
| INSR recharge complete | INSR Batt1 on status line (Table 17-25) |
| System error | Call Your Doctor Warning (Table 17-18) |
| Audio + Stop Charge | No change |
| Audio + Start Charge and hold for > 10 seconds | No change |

6—INSR Charge Status Screen
Screen Entry: User Control/System Event
  Attach DTC from Power Down Screen, Start Screen—Not Docked or Recharge INSR Warning
  Attach DTC from INSR Battery Low Message when not charging INS
  System timeout or message clear

| User Control/ System Event | System Response: Feedback/Next Screen (requirement) |
| --- | --- |
| Therapy On/Off | Telemetry success: Therapy On/Off icon on status line (Table 17-22) |
| | Telemetry event: refer to Table 18 |
| Start Charge | Antenna temperature OK: Wait Screen (Table 17-1) |
| | Antenna too hot: Antenna Too Hot Message (Table 17-30) |
| Audio | Toggle Audio icon (Table 17-24) |
| Detach DTC | Charge incomplete and not INSR battery low: INSR Recharge Interrupted Message (Table 17-10) |
| | INSR battery low: INSR Battery Low Message (Table 17-8) |
| | INSR battery depleted: Recharge INSR Warning (Table 17-9) |
| | INSR recharge complete: INSR Recharge Complete Message (Table 17-11) |
| INSR recharge complete | INSR Recharge Complete Message (Table 17-11) |
| Audio + Start Charge and hold for >10 seconds | Antenna temperature OK: Physician Recharge Screen (Table 17-21) |
| | Antenna too hot: Physician Recharge-Antenna Too Hot (Table 17-31) |
| System error | Call Your Doctor Warning (Table 17-18) |

7—Physician Recharge Screen
Screen Entry: User Control/System Event
  Audio+Start Charge and hold for >10 seconds
  Antenna temperature OK
  System timeout or message clear

| User Control/ System Event* | System Response: Feedback/Next Screen (requirement) |
| --- | --- |
| Successful communication with INS | INS Charge Status Screen (Table 17-2) |
| Timer goes to zero and: system times out (not docked) | Start Screen-Not Docked without Therapy On/Off icon on status line (Table 17-22) |
| Timer goes to zero and system times out (docked) | INSR recharge incomplete: INSR Charge Status Screen (Table 17-7) |
| | INSR recharge complete: INSR Recharge Complete Message (Table 17-11) |
| Stop Charge (not docked) | Start Screen-Not Docked |
| Stop Charge (docked) | Start Screen-Docked |

-continued

| User Control/<br>System Event* | System Response:<br>Feedback/Next Screen (requirement) |
|---|---|
| Detach DTC | INSR battery low: INSR Battery Low Message (Table 17-8)<br>INSR battery depleted: Recharge INSR Warning (Table 17-9) |
| Antenna too hot | Physician Recharge-Antenna Too Hot (Table 17-31) |
| Antenna failure | Call Your Doctor Warning (Table 17-18) |
| Antenna disconnected | Connect INSR Antenna Message (Table 17-14) |
| System error | Call Your Doctor Warning (Table 17-18) |
| INSR battery low | INSR Battery Low Message (Table 17-8) |
| INSR battery depleted | Recharge INSR Warning (Table 17-9) |
| INSR recharge complete | No change |

*Note:
all keys inactive except Stop Charge

8—IR Communication Screen
Screen Entry: User Control/System Event
  Reset button from any screen when DTC is not docked and IR command is received
Processing Requirements
  All keys inactive
  Software will display the screen until the host terminates the session, the Reset button is activated or the Audio key is pressed. (Table 17-28)
  When the host terminates the session or the Reset button is activated, software will display Start Screen—Not Docked.
9—INS Battery Low Message
Screen Entry: User Control/System Event
  Therapy On/Off

| Entry Screen | User Control/System Event: Next Screen |
|---|---|
| Power Down<br>Start Screen-<br>Not Docked | Audio key or system timeout: Start Screen-Not Docked with Therapy On/Off icon on status line (Table 17-22)<br>Therapy On/Off and telemetry success: Start Screen-Not Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Attach DTC: nochange |
| Start Screen-<br>Docked | Audio key or system timeout: Start Screen-Docked with Therapy On/Off icon on status line (Table 17-22)<br>Therapy On/Off and telemetry success: Start Screen-Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Detach DTC: no change |
| INSR Charge<br>Status | Audio key or system timeout: INSR Charge Status Screen with Therapy On/Off icon on status line (Table 17-22)<br>Therapy On/Off and telemetry success: INSR Charge Status with Therapy On/Off icon on status line (Table 17-22)<br>Therapy On/Off and telemetry event: Refer to Table 18<br>Start Charge and antenna temperature OK: Wait Screen/ INS Charge Status (Table 17-1)<br>Start Charge and antenna too hot: Antenna Too Hot Message (Table 17-30)<br>Stop Charge: no change<br>Detach DTC: nochange |

INS Battery Low Message—Continued
Screen Entry: User Control/System Event
  Stop Charge

| Entry Screen | User Control/System Event: Next Screen |
|---|---|
| INS Charge<br>Status<br>(not docked) | Audio key or system timeout: Start Screen-Not Docked<br>Therapy On/Off and telemetry success: Start Screen-Not Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Attach DTC: no change |
| INS Charge<br>Status<br>(docked) | Audio key and INSR recharge incomplete: INSR Charge Status with Therapy On/Off icon on status line (Table 17-22)<br>Audio key and INSR recharge complete: INSR Recharge Complete Message (Table 17-11)<br>Therapy On/Off and telemetry success and INSR recharge incomplete: INSR Charge Status with Therapy On/Off icon on status line (Table 17-22)<br>Therapy On/Off and telemetry success and INSR recharge complete: Start Screen-Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Detach DTC: no change |

10—INS Recharge Interrupted Message
Screen Entry: User Control/System Event
  Stop Charge

| Entry Screen | User Control/System Event: Next Screen |
|---|---|
| INS Charge<br>Status<br>(not docked) | Audio key or system timeout: Start Screen-Not Docked<br>Therapy On/Off and telemetry success: Start Screen-Not Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Attach DTC: no change |
| INS Charge<br>Status<br>(docked) | Audio key or system timeout and INSR recharge incomplete:<br>INSR Charge Status with Therapy On/Off icon on status line (Table 17-22)<br>Audio key or system timeout and INSR recharge complete: INSR Recharge Complete Message (Table 17-11)<br>Therapy On/Off and telemetry success and INSR recharge incomplete: INSR Charge Status with Therapy On/Off icon on status line (Table 17-22)<br>Therapy On/Off and telemetry success and INSR recharge complete: Start Screen-Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Detach DTC: no change |

11—INS Recharge Complete Message

Screen Entry: User Control/System Event
- Stop Charge
- INS recharge complete

| Entry Screen | User Control/System Event: Next Screen |
|---|---|
| INS Charge Status (not docked) | Audio key or system timeout: Start Screen-Not Docked<br>Therapy On/Off and telemetry success: Start Screen-Not Docked with Therapy On/Off icon on status line (Table 17-22) |
| INS Charge Status-90 to 100% (not docked) | Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Attach DTC: no change |
| INS Charge Status (docked) | Audio key or system timeout and INSR recharge incomplete: INSR Charge Status<br>Audio key or system timeout and INSR recharge complete: |
| INS Charge Status-90 to 100% (docked) | INSR Recharge Complete Message (Table 17-11)<br>Therapy On/Off and telemetry success and INSR recharge incomplete: INSR Charge Status with Therapy On/Off icon on status line (Table 17-22)<br>Therapy On/Off and telemetry success and INSR recharge complete: Start Screen-Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Detach DTC: no change |

12—INSR Battery Low Message

Screen Entry: User Control/System Event
- Therapy On/Off

| Entry Screen | User Control/System Event: Next Screen |
|---|---|
| Power Down Start Screen-Not Docked | Audio key or system timeout: Start Screen-Not Docked with Therapy On/Off icon on status line (Table 17-22)<br>Therapy On/Off and tel success: Start Screen-Not Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change |

| Entry Screen | User Control/System Event: Next Screen |
|---|---|
| INS Charge Status<br>INS Charge Status-90 to 100% | Attach DTC: INSR Charge Status with Therapy On/Off icon on status line (Table 17-23)<br>Audio key or system timeout: previous screen with Therapy On/Off icon on status line (Table 17-22)<br>Therapy On/Off and telemetry success: Wait Screen<br>Therapy On/Off and telemetry event: Refer to Table 18<br>Start Charge and antenna temperature OK: Wait Screen (Table 17-1)<br>Start Charge and antenna too hot: INS Charge Status-Antenna Too Hot Screen (Table 17-13)<br>Stop Charge: Start Screen-Not Docked<br>Attach DTC: previous screen with Therapy On/Off icon and Power Source Symbol on status line (Table 17-22, 23) |

Screen Entry: User Control/System Event
- Start Charge

| Entry Screen | User Control/System Event: Next Screen |
|---|---|
| Power Down Start Screen-Not Docked | Audio key or system timeout: Wait Screen/INS Charge Status/INS Charge Status-90 to 100%<br>Therapy On/Off and telemetry success: Wait Screen/INS Charge/INS Charge Status-90 to 100% Status with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Attach DTC: Wait Screen/INS Charge Status/INS Charge Status-90 to 100% |

INSR Battery Low Message—Continued

Screen Entry: User Control/System Event
- Audio

| Entry Screen | User Control/System Event: Next Screen |
|---|---|
| Power Down | Audio key or system timeout: Start Screen - Not Docked<br>Therapy On/Off and telemetry success: Start Screen - Not Docked with Therapy On/Off icon on status line (Table 17-22)<br>Therapy On/Off and telemetry event: Refer to Table 18<br>Attach DTC: INSR Charge Status |

Screen Entry: User Control/System Event
- INSR battery low condition

| Entry Screen | User Control/System Event: Next Screen |
|---|---|
| Wait Screen | Audio key or system timeout or Attach DTC: Wait Screen/INS Charge Status/INS Charge Status-90 to 100% |
| Physician Recharge | Audio key or system timeout or Attach DTC: Physician Recharge |
| Physician Recharge-Antenna Too Hot | Audio key or system timeout or Attach DTC: Physician Recharge-Antenna Too Hot |
| INS Charge Status | Audio key or system timeout or Attach DTC: INS Charge Status |
| INS Charge Status 90 to 100% | Audio key or system timeout or Attach DTC: INS Charge Status-90 to 100% |
| INS Charge Status-Antenna Too Hot | Audio key or system timeout or Attach DTC: INS Charge Status-Antenna Too Hot |
| Start Screen-Not Docked | Audio key or system timeout: Start Screen-Not Docked<br>Attach DTC: INSR Charge Status |

INSR Battery Low Message—Continued
Screen Entry: User Control/System Event
  Detach DTC

| Entry Screen | User Control/System Event: Next Screen |
|---|---|
| INS Charge Status | Audio key or system timeout: previous screen |
| INS Charge Status- 90 to 100% | Therapy On/Off and telemetry success: previous screen with Therapy On/Off icon on status line (Table 17-22) |
| INS Charge Status- Antenna Too Hot | Therapy On/Off and telemetry event: Refer to Table 18<br>Start Charge and antenna temperature OK: Wait Screen (Table 17-1)<br>Start Charge and antenna too hot: INS Charge Status-Antenna Too Hot Screen (Table 17-13)<br>Stop Charge: Start Screen-Not Docked<br>Attach DTC: previous screen with power source symbol on status line (Table 17-23) |
| INSR Charge Status | Audio key or system timeout: Start Screen-Not Docked<br>Therapy On/Off and telemetry success: Start Screen-Not Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Attach DTC: INSR Charge Status |
| Physician Recharge Screen | Audio key or system timeout: previous screen<br>Therapy On/Off: no change |
| Physician Recharge- Antenna Too Hot | Start Charge: no change<br>Stop Charge: Start Screen-Not Docked<br>Attach DTC: previous screen |

13—INSR Recharge Interrupted Message
Screen Entry: User Control/System Event
  Detach DTC

| Entry Screen | User Control/System Event: Next Screen |
|---|---|
| INSR Charge Status | Audio key or system timeout: Start Screen-Not Docked<br>Therapy On/Off and telemetry success: Start Screen-Not Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Attach DTC: INSR Charge Status |

14—INSR Recharge Complete Message
Screen Entry: User Control/System Event
  INSR recharge complete

| Entry Screen | User Control/System Event: Next Screen |
|---|---|
| INSR Charge Status | Audio key: Start Screen-Docked<br>Therapy On/Off and telemetry success: Start Screen-Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Detach DTC: Start Screen-Not Docked |

Screen Entry: User Control/System Event
  Attach DTC

| Entry Screen | User Control/System Event: Next Screen |
|---|---|
| Power Down<br>Start Screen - Not Docked | Audio key: Start Screen - Docked<br>Therapy On/Off and telemetry success: Start Screen - Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge: no change<br>Detach DTC: Start Screen - Not Docked |

15—INSR System Information Message
Screen Entry: User Control/System Event
  Audio+Stop Charge

| Entry Screen | User Control/System Event: Next Screen |
|---|---|
| Power Down<br>Start Screen - Not Docked<br>Start Screen - Docked | Audio key: Cycle through information<br>Stop Charge or System timeout and not docked: Start Screen - Not Docked<br>Stop Charge or System timeout and docked: Start Screen - Docked<br>Therapy On/Off and telemetry success: Start Screen - Not Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Attach/Detach DTC: no change |

16—Call Your Doctor—ERI Message
Screen Entry: User Control/System Event
  Therapy On/Off

| Entry Screen | User Control/System Event: Next Screen |
|---|---|
| Power Down<br>Start Screen - Not Docked | Audio key or system timeout: Start Screen - Not Docked with Therapy On/Off icon on status line (Table 17-22)<br>Therapy On/Off and telemetry success: Start Screen - Not Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge/Attach DTC: no change |
| INS Charge Status | Audio key or system timeout: previous screen with Therapy On/Off icon on status line (Table 17-22) |
| INS Charge Status - 90 to 100% | Therapy On/Off and telemetry success: previous screen with Therapy On/Off icon on status line (Table 17-22)<br>Therapy On/Off and telemetry event: Refer to Table 18 |
| INS Charge Status - Antenna Too Hot | Start Charge and antenna temperature OK: Wait Screen (Table 17-1)<br>Start Charge and antenna too hot: INS Charge Status - Antenna Too Hot Screen (Table 17-13) |

| Entry Screen | User Control/System Event: Next Screen |
|---|---|
| INSR Charge Status | Stop Charge and not docked: Start Screen - Not Docked<br>Stop Charge and docked: Start Screen - Docked<br>Attach DTC/Detach DTC: no change<br>Audio key or system timeout: INSR Charge Status Screen with Therapy On/Off icon on status line (Table 17-22)<br>Therapy On/Off and telemetry success: INSR Charge Status with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge/Detach DTC: no change |
| Start Screen - Docked | Audio key or system timeout: Start Screen - Docked with Therapy On/Off icon on status line (Table 17-22)<br>Therapy On/Off and telemetry success: Start Screen - Docked with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge/Detach DTC: no change |

Call Your Doctor—ERI Continued
Screen Entry: User Control/System Event
   INS error: ERI

| Entry Screen | User Control/System Event: Next Screen |
|---|---|
| Wait Screen | Audio key or system timeout: Wait Screen<br>Therapy On/Off and telemetry success: Wait Screen<br>Therapy On/Off and telemetry event: Refer to Table 18<br>Start Charge and antenna temperature OK: Wait Screen (Table 17-1)<br>Start Charge and antenna too hot: INS Charge Status - Antenna Too Hot Screen (Table 17-13)<br>Stop Charge/Attach DTC/Detach DTC: no change |
| INS Charge Status<br>INS Charge Status - 90 to 100%<br>INS Charge Status - Antenna Too Hot | Audio key or system timeout: previous screen<br>Therapy On/Off and telemetry success: previous screen with Therapy On/Off icon on status line (Table 17-22)<br>Therapy On/Off and telemetry event: Refer to Table 18<br>Start Charge and antenna temperature OK: Wait Screen (Table 17-1)<br>Start Charge and antenna too hot: INS Charge Status - Antenna Too Hot Screen (Table 17-13)<br>Stop Charge and not docked: Start Screen - Not Docked<br>Stop Charge and docked: Start Screen - Docked<br>Attach DTC/Detach DTC: no change |

17—Call Your Doctor—POR Message
Screen Entry: User Control/System Event
   Therapy On/Off

| Entry Screen | User Control/System Event: Next Screen |
|---|---|
| Power Down<br>Start Screen - Not Docked | Audio key or system timeout: Start Screen - Not Docked with Therapy On/Off icon on status line (Table 17-22)<br>Therapy On/Off: no change<br>Start Charge/Stop Charge/Attach DTC/Detach DTC: no change |
| INS Charge Status<br>INS Charge Status - 90 to 100%<br>INS Charge Status - Antenna Too Hot | Audio key or system timeout: previous screen with Therapy On/Off icon on status line (Table 17-22)<br>Therapy On/Off: no change<br>Stop Charge and not docked: Start Screen - Not Docked<br>Stop Charge and docked: Start Screen - Docked<br>Start Charge/Attach DTC/Detach DTC: no change |
| INSR Charge Status | Audio key or system timeout: INSR Charge Status Screen with Therapy On/Off icon on status line (Table 17-22)<br>Therapy On/Off: no change<br>Start Charge/Stop Charge/Attach DTC/Detach DTC: no change |
| Start Screen - Docked | Audio key or system timeout: Start Screen - Docked with Therapy On/Off icon on status line (Table 17-22)<br>Therapy On/Off: no change<br>Start Charge/Stop Charge/Attach DTC/Detach DTC: no change |

Screen Entry: User Control/System Event
   INS error: POR

| Entry Screen | User Control/System Event: Next Screen |
|---|---|
| Wait Screen | Audio key or system timeout: Wait Screen<br>Therapy On/Off and telemetry success: Wait Screen<br>Therapy On/Off and telemetry event: Refer to Table 18<br>Start Charge and antenna temperature OK: Wait Screen (Table 17-1)<br>Start Charge and antenna too hot: Antenna Too Hot Message (Table 17-30)<br>Stop Charge/Attach DTC/Detach DTC: no change |
| INS Charge Status<br>INS Charge Status - 90 to 100% INS Charge Status - Antenna Too Hot | Audio key or system timeout: previous screen<br>Therapy On/Off and telemetry success: previous screen with Therapy On/Off icon on status line (Table 17-22)<br>Therapy On/Off and telemetry event: Refer to Table 18<br>Stop Charge and not docked: Start Screen - Not Docked<br>Stop Charge and docked: Start Screen - Docked<br>Start Charge/Attach DTC/Detach DTC: no change |

18—Antenna Too Hot Message
Screen Entry: User Control/System Event
   Start Charge

| Entry Screen | User Control/System Event: Next Screen |
|---|---|
| Power Down<br>Start Screen - Docked<br>Start Screen - Not Docked<br>INSR Charge Status<br>INS Battery Low<br>INS Recharge Interrupted<br>INS Recharge Complete<br>INSR Battery Low<br>INSR Recharge Interrupted<br>INSR Recharge Complete<br>Call Your Doctor - | Audio key or system timeout and not docked and antenna too hot: Start Screen - Not Docked<br>Audio key or system timeout and docked and antenna too hot: Start Screen - Docked<br>Audio key or system timeout and docked/not docked and antenna cools: INS Charge Status/INS Charge Status - 90 to 100%<br>Therapy On/Off and telemetry success and not docked: Start Screen - Not Docked with Therapy On/Off icon on status line (Table 17-22)<br>Therapy On/Off and telemetry success and docked: Start Screen - Docked with Therapy On/Off icon on status line (Table 17-22)<br>Therapy On/Off and telemetry event: Refer to Table 18<br>Start Charge: no change<br>Stop Charge and charge complete: INS Recharge Complete Message (Table 17-6)<br>Stop Charge and charge incomplete and not INS |

| Entry Screen | User Control/System Event: Next Screen |
|---|---|
| ERI Call Your Doctor POR Reposition Antenna - Press Start Charge Warning Connect INSR Antenna | battery low: INS Recharge Interrupted Message - (Table 17-5) Stop Charge and INS battery low: INS Battery Low Message (Table 17-3) Stop Charge and INS battery depleted: Recharge Stimulator Warning (Table 17-4) Attach/detach DTC: no change |

19—Warning Messages

| Warning | User Control/System Event: Next Screen |
|---|---|
| Recharge Stimulator | Start Charge and antenna temperature OK: Wait Screen (Table 17-1) Start Charge and antenna too hot: Antenna Too Hot Message (Table 17-30) System timeout: Power Down |
| Recharge INSR | Attach DTC: INSR Charge Status Screen with Power Source Symbol System timeout: Power Down |
| Reposition Antenna - Press Start Charge | Start Charge and antenna temperature OK: Wait Screen (Table 17-1) Start Charge and antenna too hot: Antenna Too Hot Message (Table 17-30) System timeout: Power Down |
| Reposition Antenna - Press Therapy Off | Therapy Off and telemetry success: Start Screen - Docked or Start Screen - Not Docked with Therapy Off icon on status line (Table 17-22) Therapy Off and telemetry event: refer to Table 18 System timeout: Power Down |
| Reposition Antenna - Press Therapy On | Therapy On and telemetry success: Start Screen - Docked or Start Screen - Not Docked with Therapy On icon on status line (Table 17-22) Therapy On and telemetry event: refer to Table 18 System timeout: Power Down |
| Call Your Doctor | System timeout: Power Down |
| Call Your Doctor - EOS | System timeout: Power Down |

20—Splash Screen
Screen Entry: User Control/System Event
    Application is loading
    Reset button is activated and application is reloading
Processing Requirements
    All keys active
    Software will display the screen until the user presses any key or the system times out.
    When the user presses any key or the system times out, software will display the Start Screen—Docked or Start Screen—Not Docked (Table 17-29)
21—Connect INSR Antenna Message
Screen Entry: User Control/System Event
    Antenna disconnected

| Entry Screen | User Control/System Event: Next Screen (assuming antenna, and recharger are making full contact) |
|---|---|
| Wait Screen INS Charge Status Screen INS Charge Status - 90 to 100% | Audio key or system timeout and not docked: Start Screen - Not Docked Audio key or system timeout and docked: Start Screen - Docked Therapy On/Off and telemetry success and not docked: Start Screen - Not Docked with Therapy On/Off icon on status line (Table 17-22) Therapy On/Off and telemetry success and docked: Start Screen - Docked with Therapy On/Off icon on status line (Table 17-22) Therapy On/Off and telemetry event: Refer to Table 18 Start Charge and antenna temperature OK: Wait Screen (Table 17-1) Start Charge and antenna too hot: INS Charge Status - Antenna Too Hot Screen (Table 17-13) Stop Charge: no change Attach/detach DTC: no change |
| Physician Recharge Screen | Audio key or system timeout and not docked: Start Screen - Not Docked |
| Physician Recharge Screen - Antenna Too Hot | Audio key or system timeout and docked: Start Screen - Docked Therapy On/Off: no change Start Charge: no change Stop Charge: no change Attach/detach DTC: no change |

Screen Entry: User Control/System Event
    Therapy On/Off
    Start Charge

| Entry Screen | User Control/System Event: Next Screen (assuming antenna and recharger are making full contact) |
|---|---|
| All screens and messages with the exception of Physician Recharge Screen, Physician Recharge - Antenna Too Hot Screen, IR Communication Screen, Splash Screen and all reposition antenna warnings | Audio key or system timeout and not docked: Start Screen - Not Docked Audio key or system timeout and docked: Start Screen - Docked Therapy On/Off and telemetry success and not docked: Start Screen - Not Docked with Therapy On/Off icon on status line (Table 17-22) Therapy On/Off and telemetry success and docked: Start Screen - Docked with Therapy On/Off icon on status line (Table 17-22) Therapy On/Off and telemetry event: Refer to Table 18 Start Charge and antenna temperature OK: Wait Screen (Table 17-1) Start Charge and antenna too hot: Antenna Too Hot Message (Table 17-30) Stop Charge: no change Attach/detach DTC: no change |

22—INS Charge Status—90 to 100% Screen
Screen Entry: User Control/System Event
    System timeout or message clear
    Antenna temperature OK
    Battery voltage indicates 90%

| User Control/System Event | System Response: Feedback/Next Screen (requirement) |
|---|---|
| Therapy On/Off | Telemetry success: Therapy On/Off icon on status line (Table 17-22) Telemetry event: refer to Table 18 |
| Start Charge | Start Charge and antenna temperature OK: Wait Screen (Table 17-1) Start Charge and antenna too hot: INS Charge Status - Antenna Too Hot Screen (Table 17-13) |
| Stop Charge | INS Recharge Complete Message (Table 17-6) |
| Audio | Toggle Audio icon (Table 17-24) |
| Attach DTC | Power source symbol on status line (Table 17-23) |
| Detach DTC | INSR battery low: INSR Battery Low Message (Table 17-8) INSR battery depleted: Recharge INSR Warning (Table 17-9) |

-continued

| User Control/ System Event | System Response: Feedback/Next Screen (requirement) |
|---|---|
|  | Status line without power source symbol (Table 17-23) |
| INS recharge complete | INS Recharge Complete Message (Table 17-6) |
| INS error: ERI | Call Your Doctor ERI Message (Table 17-19) |
| INS error: POR | Call Your Doctor - POR Message (Table 17-27) |
| INS error: EOS, battery voltage too high | Call Your Doctor Warning (Table 17-18) |
| Antenna too hot | INS Charge Status - Antenna Too Hot (Table 17-13) |
| Antenna failure | Call Your Doctor Warning (Table 17-18) |
| Antenna disconnected | Connect INSR Antenna Message (Table 17-14) |
| INSR battery low | INSR Battery Low Message (Table 17-8) |
| INSR battery depleted | Recharge INSR Warning (Table 17-9) |
| INSR recharge complete | INSR Batt1 on status line (Table 17-25) |
| System error | Call Your Doctor Warning (Table 17-18) |
| Audio + Stop Charge | No change |
| Audio + Start Charge and hold for >10 seconds | No change |

23—INS Charge Status—Antenna Too Hot Screen

Screen Entry: User Control/System Event

Antenna too hot

System timeout or message clear

| User Control/ System Event | System Response: Feedback/Next Screen (requirement) |
|---|---|
| Therapy On/Off | Telemetry success: Therapy On/Off icon on status line (Table 17-22) |
|  | Telemetry event: refer to Table 18 |
| Start Charge | Start Charge and antenna temperature OK: Wait Screen (Table 17-1) |
|  | Start Charge and antenna too hot: INS Charge Status - Antenna Too Hot Screen (Table 17-13) |
| Stop Charge | Not docked: Start Screen - Not Docked |
|  | Docked and INSR recharge complete: INSR Recharge Complete Message (Table 17-11) |
|  | Docked and INSR recharge incomplete: INSR Charge Status Screen (Table 17-7) |
| Audio | Toggle Audio icon (Table 17-24) |
| Attach DTC | Power source symbol on status line (Table 17-23) |
| Detach DTC | INSR battery low: INSR Battery Low Message (Table 17-8) |
|  | INSR battery depleted: Recharge INSR Warning (Table 17-9) |
|  | Status line without power source symbol (Table 17-23) |
| INS error: ERI | Call Your Doctor ERI Message (Table 17-19) |
| INS error: POR | Call Your Doctor - POR Message (Table 17-27) |
| INS error: EOS, battery voltage too high | Call Your Doctor Warning (Table 17-18) |
| Antenna too hot | INS Charge Status - Antenna Too Hot (Table 17-13) |
| Antenna cooled | Wait Screen/INS Charge Status (Table 17-1) |
| Antenna failure | Call Your Doctor Warning (Table 17-18) |
| Antenna disconnected | Connect INSR Antenna Message (Table 17-14) |
| INSR battery low | INSR Battery Low Message (Table 17-8) |
| INSR battery depleted | Recharge INSR Warning (Table 17-9) |
| INSR recharge complete | INSR Batt1 on status line (Table 17-25) |
| System error | Call Your Doctor Warning (Table 17-18) |
| Audio + Stop Charge | No change |
| Audio + Start Charge and hold for >10 seconds | No change |

24—Physician Recharge—Antenna Too Hot Screen

Screen Entry: User Control/System Event

Antenna too hot

| User Control/ System Event* | System Response: Feedback/Next Screen (requirement) |
|---|---|
| Successful communication with INS | INS Charge Status Screen (Table 17-2) |
| Timer goes to zero and system times out (not docked) | Start Screen - Not Docked without Therapy On/Off icon on status line (Table 17-22) |
| Timer goes to zero and system times out (docked) | INSR recharge incomplete: INSR Charge Status Screen (Table 17-7) |
|  | INSR recharge complete: INSR Recharge Complete Message (Table 17-11) |
| Stop Charge (not - docked) | Start Screen - Not Docked |
| Stop Charge (docked) | Start Screen - Docked |
| Detach DTC | INSR battery low: INSR Battery Low Message (Table 17-8) |
|  | INSR battery depleted: Recharge INSR Warning (Table 17-9) |
| Antenna too hot | Physician Mode - Antenna Too Hot (Table 17-31) |
| Antenna failure | Call Your Doctor Warning (Table 17-18) |
| Antenna disconnected | Connect INSR Antenna Message (Table 17-14) |
| System error | Call Your Doctor Warning (Table 17-18) |
| INSR battery low | INSR Battery Low Message (Table 17-8) |
| INSR battery depleted | Recharge INSR Warning (Table 17-9) |
| INSR recharge complete | No change |

*Note:
all keys inactive except Stop Charge

TABLE 6

1- When the user presses start charge or the antenna has cooled, software will display the Wait Screen until successful communication with the INS is established.
2- Software will display the INS Charge Status Screen as soon as successful communication with the INS is established.
3- Display INS Battery Low Message
4- Display Recharge Stimulator Warning
5- Display INS Recharge Interrupted Message
6- Display INS Recharge Complete Message
7- Display INSR Charge Status Screen
8- Display INSR Battery Low Message
9- Display Recharge INSR Warning
10- Display INSR Recharge Interrupted Message
11- Display INSR Recharge Complete Message
12- Display Reposition Antenna Press Start Charge Warning
13- Display INS Charge Status - Antenna Too Hot Screen
14- Display Connect INSR Antenna Message
15- Display Reposition Antenna Press Therapy On Warning
16- Display Reposition Antenna Press Therapy Off Warning
17- Display INSR System Information Message
18- Display Call Your Doctor Warning
19- Display Call Your Doctor - ERI Message
20- Entry intentionally left blank to preserve numbering
21- Display Physician Recharge Screen
22- Software will display an indicator for stimulation status (On/Off) on the status line.
23- Software will display the power source symbol when the desktop charger is docked.
24- Software will display an indicator for audio control on the status line.
25- Software will display the INSR charge level on the status line.
26- Software will update the recharge efficiency line each time user presses Start Charge.
27- Display Call Your Doctor - POR Message
28- Display IR Communication Screen
29- Display Splash Screen
30- Display Antenna Too Hot Message
31- Display Physician Recharge - Antenna Too Hot Screen

TABLE 7

Therapy On/Off Events

| System Event | Next Screen (requirement) |
| --- | --- |
| 1. Telemetry failure for Therapy On | Reposition Antenna - Press Therapy On Warning (Table 17-15) |
| 2. Telemetry failure for Therapy Off | Reposition Antenna - Press Therapy Off Warning (Table 17-16) |
| 3. INS battery low | INS Battery Low Message (Table 17-3) |
| 4. INS battery depleted or in sleep mode | Recharge Stimulator Warning (Table 17-4) |
| 5. INS error - ERI | Call Your Doctor - ERI Message (Table 17-19) |
| 6. INS error - POR | Call Your Doctor - POR Message (Table 17-27) |
| 7. INS error - EOS or battery voltage too high | Call Your Doctor Warning (Table 17-18) |
| 8. INSR battery low | INSR Battery Low Message (Table 17-8) |
| 9. INSR battery depleted | Recharge INSR Warning (Table 17-9) |
| 10. Antenna failure | Call Your Doctor Warning (Table 17-18) |
| 11. Antenna disconnected | Connect INSR Antenna Message (Table 17-14) |
| 12. System error | Call Your Doctor Warning (Table 17-18) |
| 13. Antenna too hot | Display INS Charge Status - Antenna Too Hot Screen (Table 17-13) or Antenna Too Hot Message (Table 17-30) |

User familiarity with both external programming unit 2 and charging unit 50 is enhanced through the use of common patient controls and/or display icons across both devices. The user is presented with common controls and displays across both platforms.

The primary purpose of external programming unit 2 is to manipulate therapeutic programs such as starting therapy and stopping therapy. The primary purpose of charging unit 50 is to charge or recharge rechargeable power source 24. However, patients may want to control their therapy while charging unit 50 is charging the rechargeable power source 24 of implantable medical device 16. Thus, charging unit 50 is also equipped with controls to start and stop therapy as well as controls to start and stop charging.

External programming unit 2 and charging unit 50 both have similar "Therapy On" controls as illustrated in Table 1 and Table 11, respectively. Similarly, both external programming unit 2 and charging unit 50 also have similar "Therapy Off" controls as illustrated in Table 1 and Table 11, respectively.

To aid in familiarity by the user, both external programming unit 2 and charging unit 50 also have similar or identical icons to display the same or similar messages to the user. Battery charging level icons "INSR Batt 1", "INSR Batt 2", "INSR Batt 3", "INSR Batt 4" and "INSR Batt 5" icons are similar or identical between external programming unit 2 and charging unit 50 as illustrated in Table 1 and Table 11, respectively.

Similarly, the "Call Doctor" icon illustrated in Table 5 with respect to external programming unit 2 is the same as, or very nearly the same as, the "Call Doctor" icon illustrated in Table 15 with respect to charging unit 50.

The "Warnings" icon illustrated in Table 5 with respect to external programming unit 2 is the same as, or very nearly the same as, the "Warnings" icon illustrated in Table 16 with respect to charging unit 50.

"Audio On" and "Audio Off" icons illustrated in Table 6 with respect to external programming unit 2 are the same as, or very nearly the same as, the "Audio On" and "Audio Off" icons illustrated in Table 11 with respect to charging unit 50.

These are examples of controls and icons that are the same, or very similar, between both platforms, the external programming unit 2 and the charging unit 50 to aid in user familiarity.

As noted with respect to FIG. 17 describing the process of charging rechargeable power source 24 using external charging device 48, charging unit 50 receives information via telemetry from implantable medical device 16 during the charging process. External antenna 52 contains both primary coil 54 and external telemetry coil 46 and implantable medical device 16 contains both secondary coil 34 and internal telemetry coil 44. When external antenna 52 is positioned properly at or near the site of implantable medical device 16, primary coil 54 can be inductively coupled to secondary coil 34 to facilitate the charging process. Similarly, external telemetry coil 46 can be coupled with internal telemetry coil 44 to communicate information across cutaneous boundary 38 during the charging process.

Also as noted above, magnetic shield 36 prevent electromagnetic radiation stimulating secondary coil 34 from reaching the interior of housing 32 of implantable medical device. However, external telemetry coil 46 and internal telemetry coil 44 are sized to be larger than magnetic shield 36 allowing electromagnetic communication between external telemetry coil 46 and internal telemetry coil 44.

At step 112 of the charging process illustrated in FIG. 17, a check is made to determine if telemetry between charging unit 50 and implantable medical device 16. Further, the status of charging rechargeable power source 24 is communicated from implantable medical device 16 and displayed by charging unit 50 (step 118). The charging status displayed by charging unit 50 can be the actual known charging status of rechargeable power source 24 as communicated from implantable medical device 16 to charging unit 50. This prevents essentially guessing the internal charging status of rechargeable power source 24 by some external means such as simply by the passage of time. Rather, the actual charging status of rechargeable power source 24, e.g., the battery voltage, can be measured and transmitted to charging unit 50 for display to the user.

Typically, inductive charging and telemetry operations are time division multiplexed during the charging operation. That is, a portion of the time during which charging occurs is dedicated to telemetry. During this dedicated telemetry time, the inductive charging by primary coil 54 to secondary coil 34 is momentarily stopped and telemetry allowed to occur. As soon as telemetry has occurred and the required information has been communicated, inductive coupling can be resumed. Typically, only a relatively small portion of the time period during charging is required to be devoted to telemetry. Inductive charging can be stopped only for a short, e.g., a few seconds, to allow for telemetry and then inductive charging can be resumed. Although the time division multiplexing occurs over the entire charging period, only a small portion of the charging time is lost to telemetry. Time division multiplexing of inductive coupling charging and telemetry prevents the possibility of inductive charging from interfering with telemetry signals.

Thus, embodiments of the user interface for external charger for implantable medical device are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device system, comprising:
    an implantable medical device for providing a therapeutic output to a patient;
    an external patient control unit which can be operatively coupled via telemetry with said implantable medical device allowing said patient to control said therapeutic output of said implantable medical device; and an external energy transfer unit which can be operatively coupled to said implantable medical device to transcutaneously transfer energy to said implantable medical device;

said external patient control unit having a first user interface operable by said patient having patient controls and display icons indicative of a status of operation of said patient control unit;

said energy transfer unit having a second user interface that is separate from the first user interface and that is operable by said patient having patient controls and display icons indicative of a status of operation of said energy transfer unit;

at least some of said patient controls and said display icons of said energy transfer unit being common with at least some of said patient controls and said display icons of said patient control unit.

2. A system as in claim 1 wherein at least one of said display icons comprises an icon representative of a state of charging of an energy storage device in said implantable medical device.

3. A system as in claim 1 wherein at least one of said patient controls comprises a control for adjusting said therapeutic output of said implantable medical device.

4. A system as in claim 1 wherein said external energy transfer unit inductively couples energy to said implantable medical device.

5. A system as in claim 1 wherein said implantable medical device has a rechargeable energy storage device and wherein said energy transfer unit charges said rechargeable energy storage device.

6. An external energy transfer unit adapted to transcutaneously transfer energy to an implantable medical device for providing a therapeutic output to a patient, said implantable medical device capable of communication with an external patient control unit allowing said patient to control said therapeutic output of said implantable medical device, said external patient control unit having a first user interface operable by said patient having patient controls and display icons indicative of a status of operation of said patient control unit, comprising:

a second user interface that is separate from the first user interface and that is operable by said patient having patient controls and display icons indicative of a status of operation of said energy transfer unit;

at least some of said patient controls and said display icons of said energy transfer unit being common with at least some of said patient controls and said display icons of said patient control unit.

7. An external energy transfer unit as in claim 6 wherein at least one of said display icons comprises an icon representative of a state of charging of an energy storage device in said implantable medical device.

8. An external energy transfer unit as in claim 6 wherein at least one of said patient controls comprises a control for adjusting said therapeutic output of said implantable medical device.

9. An external energy transfer unit as in claim 6 wherein said external energy transfer unit inductively couples energy to said implantable medical device.

10. An external energy transfer unit as in claim 6 wherein said implantable medical device has a rechargeable energy storage device and wherein said energy transfer unit charges said rechargeable energy storage device.

11. A method of providing therapeutic output to a patient using an implantable medical device, comprising the steps of:

operatively coupling via telemetry an external patient control unit with said implantable medical device allowing said patient to control said therapeutic output of said implantable medical device; and operatively coupling an external energy transfer unit to said implantable medical device to transcutaneously transfer energy to said implantable medical device;

said external patient control unit having a first user interface operable by said patient having patient controls and display icons indicative of a status of operation of said patient control unit;

said energy transfer unit having a second user interface that is separate from the first user interface and that is operable by said patient having patient controls and display icons indicative of a status of operation of said energy transfer unit;

at least some of said patient controls and said display icons of said energy transfer unit being common with at least some of said patient controls and said display icons of said patient control unit.

12. A method as in claim 11 wherein at least one of said displays icons comprises an icon representative of a state of charging of an energy storage device in said implantable medical device.

13. A method as in claim 11 wherein at least one of said patient controls comprises a control for adjusting said therapeutic output of said implantable medical device.

14. A method as in claim 11 wherein said external energy transfer unit inductively couples energy to said implantable medical device.

15. A method as in claim 11 wherein said implantable medical device has a rechargeable energy storage device and wherein said energy transfer unit charges said rechargeable energy storage device.

16. An implantable medical device system, comprising:
an implantable medical device for providing a therapeutic output to a patient; and an external energy transfer unit which can be operatively coupled to transcutaneously transfer energy to said implantable medical device, the external energy transfer unit including a housing and electronics within the housing that provides oscillating current to provide the energy being transferred to said implantable medical device;

said energy transfer unit being operable by said patient with at least one and less than three operative controls to control energy transfer from said external energy transfer unit to said implantable medical device, said energy transfer unit including the controls on the housing.

17. A system as in claim 16 wherein said energy transfer unit is operable with two operative controls to control energy transfer from said external energy transfer unit to said implantable medical device.

18. A system as in claim 17 wherein said two operative controls comprise a start control and a stop control.

19. A system as in claim 18 wherein said start control is a start button and wherein said stop control is a stop button.

20. A system as in claim 16 wherein said energy transfer unit further comprises operative controls to start and stop said therapeutic output of said implantable medical device.

21. A system as in claim 16 wherein said energy transfer unit further comprises a control to enable and silence audio feedback from said energy transfer unit.

22. A system as in claim 16 wherein said external energy transfer unit inductively couples energy to said implantable medical device.

23. A system as in claim 16 wherein said implantable medical device has a rechargeable energy storage device and wherein said energy transfer unit charges said rechargeable energy storage device.

24. An external energy transfer unit adapted to transcutaneously transfer energy to an implantable medical device for providing a therapeutic output to a patient, comprising:
a housing;
energy transfer circuitry including electronics within the housing that provides oscillating current to provide the energy being transcutaneously transferred to said implantable medical device; and
at least one and less than three operative controls on the housing to control energy transfer from said external energy transfer unit to said implantable medical device.

25. An external energy transfer unit as in claim 24 wherein said less than three operative controls comprises two operative controls to control energy transfer from said external energy transfer unit to said implantable medical device.

26. An external energy transfer unit as in claim 25 wherein said two operative controls comprise a start control and a stop control.

27. An external energy transfer unit as in claim 26 wherein said start control is a start button and wherein said stop control is a stop button.

28. An external energy transfer unit as in claim 24 wherein said energy transfer unit further comprises operative controls to start and stop said therapeutic output of said implantable medical device.

29. An external energy transfer unit as in claim 24 wherein said energy transfer unit further comprises a control to enable and silence audio feedback from said energy transfer unit.

30. An external energy transfer unit as in claim 24 wherein said external energy transfer unit inductively couples energy to said implantable medical device.

31. An external energy transfer unit as in claim 24 wherein said implantable medical device has a rechargeable energy storage device and wherein said energy transfer unit charges said rechargeable energy storage device.

32. A method for providing a therapeutic output to a patient with an implantable medical device, comprising the steps of:
operatively coupling an external energy transfer unit with said implantable medical device to transcutaneously transfer energy to said implantable medical device, wherein the external energy transfer unit includes electronics within a housing that provide oscillating current to provide the energy; and
controlling said energy transfer unit with at least one and less than three operative controls located on the housing to control energy transfer from said external energy transfer unit to said implantable medical device.

33. A method as in claim 32 wherein said controlling step is accomplished with two operative controls.

34. A method as in claim 33 wherein said two operative controls comprise a start control and a stop control.

35. A method as in claim 34 wherein said start control is a start button and wherein said stop control is a stop button.

36. A method as in claim 32 further comprising the step of controlling said energy transfer unit to start and stop said therapeutic output of said implantable medical device.

37. A method as in claim 32 further comprising the step of controlling said energy transfer unit to enable and silence audio feedback from said energy transfer unit.

38. A method as in claim 32 further comprising the step of inductively coupling energy to said implantable medical device.

39. A method as in claim 32 wherein said implantable medical device has a rechargeable energy storage device and wherein said energy transfer unit charges said rechargeable energy storage device.

40. An implantable medical device system, comprising:
an implantable medical device for providing a therapeutic output to a patient, said implantable medical device capable of receiving inductively coupled energy with a secondary coil and being capable of being transcutaneously controlled using an internal telemetry coil; and
an external antenna providing a structure having a primary coil adapted to inductively transfer energy to said secondary coil of said implantable medical device when said external antenna is externally placed in proximity of said secondary coil and having an external telemetry coil adapted to inductively transfer data to said internal telemetry coil when said external antenna is externally placed in proximity of said internal telemetry coil;
an external energy transfer unit adapted to be operatively coupled by a cord to said external antenna, said external energy transfer unit driving said primary coil to inductively transfer energy to said implantable medical device and adapted to at least partially control said therapeutic output of said implantable medical device by communicating through said external telemetry coil.

41. A system as in claim 40 wherein said energy transfer unit can control said implantable medical device to turn said therapeutic output on and off.

42. A system as in claim 40 wherein said energy transfer unit can control said implantable medical device using said external telemetry coil while transferring energy to said implantable medical using said primary coil of said antenna.

43. A system as in claim 40 wherein said implantable medical device has a rechargeable energy storage device and wherein said energy transfer unit charges said rechargeable energy storage device.

44. An external energy transfer system adapted to transcutaneously transfer energy to an implantable medical device for providing a therapeutic output to a patient, said implantable medical device capable of receiving inductively coupled energy with a secondary coil and being capable of being transcutaneously controlled using an internal telemetry coil, comprising:
an external antenna providing a structure having a primary coil adapted to inductively transfer energy to said secondary coil of said implantable medical device when said external antenna is externally placed in proximity of said secondary coil and having an external telemetry coil adapted to inductively transfer data to said internal telemetry coil when said external antenna is externally placed in proximity of said internal telemetry coil; and
an external energy transfer unit adapted to be operatively coupled by a cord to said external antenna, said external energy transfer unit driving said primary coil to inductively transfer energy to said implantable medical device and adapted to at least partially control said therapeutic output of said implantable medical device by communicating through said external telemetry coil;

said energy transfer unit having an external telemetry coil allowing said energy transfer unit to communicate with said implantable medical device through said internal telemetry coil in order to at least partially control said therapeutic output of said implantable medical device.

45. An external energy transfer system as in claim 44 wherein said energy transfer unit can control said implantable medical device to turn said therapeutic output on and off.

46. An external energy transfer system as in claim 44 wherein said energy transfer unit can control said implantable medical device using said external telemetry coil while transferring energy to said implantable medical using said primary coil of said antenna.

47. An external energy transfer system as in claim 44 wherein said implantable medical device has a rechargeable energy storage device and wherein said energy transfer unit charges said rechargeable energy storage device.

48. A method of controlling an implantable medical device for providing a therapeutic output, said implantable medical device capable of receiving inductively coupled energy with a secondary coil and being capable of being transcutaneously controlled using an internal telemetry coil, comprising the steps of:

inductively transferring energy to said secondary coil with a primary coil of an external antenna that provides a structure having the primary coil when said external antenna is externally placed in proximity of said secondary coil;

driving said primary coil with an external energy transfer unit operatively coupled by a cord to said external antenna to inductively transfer energy to said implantable medical device; and communicating with an external telemetry coil of said energy transfer unit, where the structure of the external antenna includes the external telemetry coil, with said implantable medical device through said internal telemetry coil in order to at least partially control said therapeutic output of said implantable medical device.

49. A method as in claim 48 wherein said communicating step is operable to turn said therapeutic output on and off.

50. A method as in claim 48 wherein said inductively transferring step and said communicating step occur simultaneously.

51. A method as in claim 48 wherein said implantable medical device has a rechargeable energy storage device and wherein said energy transfer unit charges said rechargeable energy storage device.

* * * * *